(12) United States Patent
Togino

(10) Patent No.: US 6,510,006 B1
(45) Date of Patent: Jan. 21, 2003

(54) IMAGE-FORMING OPTICAL SYSTEM

(75) Inventor: Takayoshi Togino, Koganei (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/417,917

(22) Filed: Oct. 13, 1999

(30) Foreign Application Priority Data

Dec. 7, 1998 (JP) .......................... 10-347282

(51) Int. Cl.[7] .................. G02B 5/04; G02B 27/14; A61B 1/06; G03B 7/099; G03B 13/02
(52) U.S. Cl. .................. 359/631; 359/633; 359/637; 359/824; 348/65; 348/68; 396/17; 396/84; 396/111; 396/148; 396/172; 396/384; 600/160; 600/178
(58) Field of Search .................. 359/631, 633, 359/637, 834, 835; 348/65, 68; 396/17, 79, 84, 111, 148, 172, 384; 600/160, 178

(56) References Cited

U.S. PATENT DOCUMENTS

| | | | | |
|---|---|---|---|---|
| 5,768,025 A | * | 6/1998 | Togino et al. | 359/633 |
| 5,815,326 A | * | 9/1998 | Takahashi | 359/633 |
| 5,936,773 A | * | 8/1999 | Togino | 359/631 |
| 5,991,103 A | * | 11/1999 | Togino | 359/834 |
| 6,128,137 A | * | 10/2000 | Togino | 359/631 |
| 6,178,052 B1 | * | 1/2001 | Aoki et al. | 359/631 |
| 6,201,646 B1 | * | 3/2001 | Togino et al. | 359/631 |
| 6,222,676 B1 | * | 4/2001 | Togino et al. | 359/631 |
| 6,259,564 B1 | * | 7/2001 | Kamo | 359/633 |
| 6,268,963 B1 | * | 7/2001 | Akiyama | 359/631 |
| 6,342,871 B1 | * | 1/2002 | Takeyama | 359/631 |

FOREIGN PATENT DOCUMENTS

| | | |
|---|---|---|
| JP | 8-292371 | 11/1996 |
| JP | 10-20196 | 1/1998 |
| JP | 10-6886 | 3/1998 |
| JP | 10-68884 | * 10/1998 |

OTHER PUBLICATIONS

Patent Abstracts of Japan, Jun. 23, 2000, JP 2000–171714, Application No. 10–347282.*

* cited by examiner

Primary Examiner—Ricky D. Shafer
(74) Attorney, Agent, or Firm—Pillsbury Winthrop LLP

(57) ABSTRACT

A high-performance image-forming optical system made compact and thin by folding an optical path using reflecting surfaces arranged to minimize the number of reflections. The image-forming optical system has a single prism. When image-side three surfaces of the prism are defined as a surface A, a surface B and a surface C in order from the image plane side thereof, at least one of the surfaces B and C has a rotationally asymmetric curved surface configuration that gives a power to a light beam and corrects aberrations due to decentration. The optical system leads light rays from an object to the image plane without forming an image in the prism and has a pupil in the prism. The surface A is a transmitting surface through which rays exit from the prism. The surfaces B and C are internally reflecting surfaces. Rays incident on the surface C and rays reflected from the surface B intersect each other in the prism.

28 Claims, 14 Drawing Sheets

45 Shutter
46 Flash
43 Finder optical system
40 Camera
44 Optical path for finder
41 Photographic optical system
42 Optical path for photography 40 Camera
45 Shutter
44 Optical path for finder
47 Liquid crystal display monitor

IMAGE-FORMING OPTICAL SYSTEM

BACKGROUND OF THE INVENTION

The present invention relates to image-forming optical systems. More particularly, the present invention relates to a decentered optical system with a reflecting surface having a power for use in optical apparatus using a small-sized image pickup device, e.g. video cameras, digital still cameras, film scanners, and endoscopes.

Recently, with the achievement of small-sized image pickup devices, image-forming optical systems for use in video cameras, digital still cameras, film scanners, endoscopes, etc. have also been demanded to be reduced in size and weight and also in cost.

In the general rotationally symmetric coaxial optical systems, however, optical elements are arranged in the direction of the optical axis. Therefore, there is a limit to the reduction in thickness of the optical systems. At the same time, the number of lens elements unavoidably increases because it is necessary to correct chromatic aberration produced by a rotationally symmetric refracting lens used in the optical systems. Therefore, it is difficult to reduce the cost in the present state of the art. Under these circumstances, there have recently been proposed optical systems designed to be compact in size by giving a power to a reflecting surface, which produces no chromatic aberration, and folding an optical path in the optical axis direction.

Japanese Patent Application Unexamined Publication (KOKAI) Number [hereinafter referred to as "JP(A)"] 7-333505 proposes to reduce the thickness of an optical system by giving a power to a decentered reflecting surface and thus folding an optical path. In an example thereof, however, the number of constituent optical members is as large as five, and actual optical performance is unclear. No mention is made of the configuration of the reflecting surface.

JP(A) 8-292371, 9-5650 and 9-90229 each disclose an optical system in which an optical path is folded by a single prism or a plurality of mirrors integrated into a single block, and an image is relayed in the optical system to form a final image. In these conventional examples, however, the number of reflections increases because the image is relayed. Accordingly, surface accuracy errors and decentration accuracy errors are transferred while being added up. Consequently, the accuracy required for each surface becomes tight, causing the cost to increase unfavorably. The relay of the image also causes the overall volumetric capacity of the optical system to increase unfavorably.

JP(A) 9-222563 discloses an example of an optical system that uses a plurality of prisms. However, because the optical system is arranged to relay an image, the cost increases and the optical system becomes large in size unfavorably for the same reasons as stated above.

JP(A) 9-211331 discloses an example of an optical system in which an optical path is folded by using a single prism to achieve a reduction in size of the optical system. However, the optical system is not satisfactorily corrected for aberrations.

JP(A) 8-292368, 8-292372, 9-222561, 9-258105 and 9-258106 all disclose examples of zoom lens systems. In these examples, however, the number of reflections is undesirably large because an image is relayed in a prism. Therefore, surface accuracy errors and decentration accuracy errors of reflecting surfaces are transferred while being added up, unfavorably. At the same time, the overall size of the optical system unavoidably increases, unfavorably.

JP(A) 10-20196 discloses an example of a two-unit zoom lens system having a positive front unit and a negative rear unit, in which the positive front unit comprises a prism of negative power placed on the object side of a stop and a prism of positive power placed on the image side of the stop. JP (A) 10-20196 also discloses an example in which the positive front unit, which comprises a prism of negative power and a prism of positive power, is divided into two to form a three-unit zoom lens system having a negative unit, a positive unit and a negative unit. However, the prisms used in these examples each have two transmitting surfaces and two reflecting surfaces, which are all independent surfaces. Therefore, a relatively wide space must be ensured for the prisms. In addition, the image plane is large in size in conformity to the Leica size film format. Accordingly, the prisms themselves become unavoidably large in size. Furthermore, because the disclosed zoom lens systems are not telecentric on the image side, it is difficult to apply them to image pickup devices such as CCDs. In either of the examples of zoom lens systems, zooming is performed by moving the prisms. Accordingly, the decentration accuracy required for the reflecting surfaces becomes tight in order to maintain the required performance over the entire zooming range, resulting in an increase in the cost.

When a general refracting optical system is used to obtain a desired refracting power, chromatic aberration occurs at an interface surface thereof according to chromatic dispersion characteristics of an optical element. To correct the chromatic aberration and also correct other ray aberrations, the refracting optical system needs a large number of constituent elements, causing the cost to increase. In addition, because the optical path extends straight along the optical axis, the entire optical system undesirably lengthens in the direction of the optical axis, resulting in an unfavorably large-sized image pickup apparatus.

In decentered optical systems such as those described above in regard to the prior art, an imaged figure or the like is undesirably distorted and the correct shape cannot be reproduced unless the formed image is favorably corrected for aberrations, particularly rotationally asymmetric distortion.

Furthermore, in a case where a reflecting surface is used in a decentered optical system, the sensitivity to decentration errors of the reflecting surface is twice as high as that in the case of a refracting surface, and as the number of reflections increases, decentration errors that are transferred while being added up increase correspondingly. Consequently, manufacturing accuracy and assembly accuracy, e.g. surface accuracy and decentration accuracy, required for reflecting surfaces become even more strict.

SUMMARY OF THE INVENTION

In view of the above-described problems of the prior art, an object of the present invention is to provide a high-performance and low-cost image-forming optical system having a reduced number of constituent optical elements.

Another object of the present invention is to provide a high-performance image-forming optical system that is made compact and thin by folding an optical path using reflecting surfaces arranged to minimize the number of reflections.

To attain the above-described objects, the present invention provides an image-forming optical system having a positive refracting power as a whole for forming an object image. The image-forming optical system has at least one prism formed from a medium having a refractive index (n) larger than 1.3 (n>1.3). The prism has at least four optical surfaces that transmit or reflect a light beam. When image-side three surfaces of the at least four optical surfaces are defined as a surface A, a surface B and a surface C in order from the image plane side of the prism, at least one of the surfaces B and C has a curved surface configuration that gives a power to a light beam. The curved surface configuration has a rotationally asymmetric surface configuration that corrects aberrations due to decentration. The image-forming optical system leads light rays from an object to the image plane without forming an image in the prism and has a pupil in the prism. The surface A has a transmitting action by which rays internally reflected from the surface B are allowed to exit from the prism. The surface B has a reflecting action to reflect rays internally reflected from the surface C. The surface C has a reflecting action. Rays incident on the surface C and the rays reflected from the surface B intersect each other.

The reasons for adopting the above-described arrangement in the present invention, together with the function thereof, will be described below in order.

The image-forming optical system according to the present invention, which is provided to attain the above-described objects, has a positive refracting power as a whole for forming an object image. The image-forming optical system has at least one prism formed from a medium having a refractive index (n) larger than 1.3 (n>1.3). The prism has at least four optical surfaces that transmit or reflect a light beam. The image-forming optical system leads light rays from an object to the image plane without forming an image in the prism and has a pupil in the prism.

A refracting optical element such as a lens is provided with a power by giving a curvature to an interface surface thereof. Accordingly, when rays are refracted at the interface surface of the lens, chromatic aberration unavoidably occurs according to chromatic dispersion characteristics of the refracting optical element. Consequently, the common practice is to add another refracting optical element for the purpose of correcting the chromatic aberration.

Meanwhile, a reflecting optical element such as a mirror or a prism produces no chromatic aberration in theory even when a reflecting surface thereof is provided with a power, and need not add another optical element only for the purpose of correcting chromatic aberration. Accordingly, an optical system using a reflecting optical element allows the number of constituent optical elements to be reduced from the viewpoint of chromatic aberration correction in comparison to an optical system using a refracting optical element.

At the same time, a reflecting optical system using a reflecting optical element allows the optical system itself to be compact in size in comparison to a refracting optical system because the optical path is folded in the reflecting optical system.

Reflecting surfaces require a high degree of accuracy for assembly and adjustment because they have high sensitivity to decentration errors in comparison to refracting surfaces. However, among reflecting optical elements, prisms, in which the positional relationship between surfaces is fixed, only need to control decentration as a single unit of prism and do not need high assembly accuracy and a large number of man-hours for adjustment as are needed for other reflecting optical elements.

Furthermore, a prism has an entrance surface and an exit surface, which are refracting surfaces, and a reflecting surface. Therefore, the degree of freedom for aberration correction is high in comparison to a mirror, which has only a reflecting surface. In particular, if the prism reflecting surface is assigned the greater part of the desired power to thereby reduce the powers of the entrance and exit surfaces, which are refracting surfaces, it is possible to reduce chromatic aberration to a very small quantity in comparison to refracting optical elements such as lenses while maintaining the degree of freedom for aberration correction at a high level in comparison to mirrors. Furthermore, the inside of a prism is filled with a transparent medium having a refractive index higher than that of air. Therefore, it is possible to obtain a longer optical path length than in the case of air. Accordingly, the use of a prism makes it possible to obtain an optical system that is thinner and more compact than those formed from lenses, mirrors and so forth, which are placed in the air.

In addition, an image-forming optical system is required to exhibit favorable image-forming performance as far as the peripheral portions of the image field, not to mention the performance required for the center of the image field. In the case of a general coaxial optical system, the sign of the ray height of extra-axial rays is inverted at a stop. Accordingly, if optical elements are not in symmetry with respect to the stop, off-axis aberrations are aggravated. For this reason, the common practice is to place refracting surfaces at respective positions facing each other across the stop, thereby obtaining a satisfactory symmetry with respect to the stop, and thus correcting off-axis aberrations.

For the reasons stated above, the present invention adopts a basic arrangement in which the image-forming optical system has a stop in the prism and does not form an intermediate image. In addition, it is desirable that the image-forming optical system should be approximately telecentric on the image side.

Next, the arrangement of an image-forming optical system that is approximately telecentric on the image side will be described in detail.

As has been stated above, reflecting surfaces have a high decentration error sensitivity in comparison to refracting surfaces. Therefore, it is desirable to provide an arrangement of an optical system that is as independent of the high decentration error sensitivity as possible. In the case of a general coaxial optical system arranged to be approximately telecentric on the image side, because extra-axial principal rays are approximately parallel to the optical axis, the positional accuracy of the extra-axial rays is satisfactorily maintained on the image plane even if defocusing is effected. Therefore, the image-forming optical system according to the present invention is arranged to reflect the property of the above-described arrangement. In particular, to prevent the performance of an optical system using a reflecting surface, which has a relatively high decentration error sensitivity, from being deteriorated by focusing, it is desirable to adopt an arrangement in which the optical system is approximately telecentric on the image side, whereby the positional accuracy of extra-axial rays is maintained favorably.

Such an arrangement enables the present invention to be suitably applied to an image pickup optical system using an image pickup device, e.g. a CCD, in particular. Adopting the above-described arrangement minimizes the influence of the cosine fourth law. Accordingly, it is also possible to reduce shading.

As has been stated above, adopting the basic arrangement of the present invention makes it possible to obtain a compact image-forming optical system that has a smaller number of constituent optical elements than in the case of a refracting optical system and exhibits favorable performance throughout the image field, from the center to the periphery thereof.

Incidentally, the prism in the present invention has an image-side part including reflecting and transmitting surfaces. That is, the image-side part of the prism includes a surface C that reflects in the prism a light beam passing through a first transmitting surface placed in a front-half part of the prism to allow a light beam to enter the prism (in a case where another reflecting surface is provided, the surface C reflects the light beam reflected from the reflecting surface). The surfaces in the image-side part of the prism further include a surface B that reflects in the prism the light beam reflected from the surface C, and a surface A through which the light beam exits from the prism. At least one of the surfaces B and C has a curved surface configuration that gives a power to a light beam. The curved surface configuration has a rotationally asymmetric surface configuration that corrects aberrations due to decentration.

An object-side part of the prism in the present invention, exclusive of the surfaces A, B and C, has at least one reflecting surface that reflects a light beam in the prism (the object-side part will hereinafter be referred to as the "prism object-side part", and the part including the surfaces A, B and C as the "prism image-side part"). The reflecting surface has a rotationally asymmetric surface configuration that gives a power to a light beam and corrects aberrations due to decentration.

When a light ray from the object center that passes through the center of the stop and reaches the center of the image plane is defined as an axial principal ray, it is desirable that the at least one reflecting surface in the prism object-side part should be decentered with respect to the axial principal ray. If the at least one reflecting surface in the prism object-side part is not decentered with respect to the axial principal ray, the axial principal ray travels along the same optical path when incident on and reflected from the reflecting surface, and thus the axial principal ray is intercepted in the optical system undesirably. As a result, an image is formed from only a light beam whose central portion is shaded. Consequently, the center of the image is unfavorably dark, or no image is formed in the center of the image field.

It is also possible to decenter a reflecting surface with a power with respect to the axial principal ray.

When a reflecting surface with a power is decentered with respect to the axial principal ray, it is desirable that at least one of surfaces constituting the prism used in the present invention should be a rotationally asymmetric surface. In the prism image-side part, it is particularly preferable from the viewpoint of aberration correction that at least one of the surfaces C and B, which are reflecting surfaces, should be a rotationally asymmetric surface. In the prism object-side part, it is particularly preferable from the viewpoint of aberration correction that the at least one reflecting surface should be a rotationally asymmetric surface.

The reasons for adopting the above-described arrangements in the present invention will be described below in detail.

First, a coordinate system used in the following description and rotationally asymmetric surfaces will be described.

An optical axis defined by a straight line along which the axial principal ray travels until it intersects the first surface of the optical system is defined as a Z-axis. An axis perpendicularly intersecting the Z-axis in the decentration plane of each surface constituting the image-forming optical system is defined as a Y-axis. An axis perpendicularly intersecting the optical axis and also perpendicularly intersecting the Y-axis is defined as an X-axis. Ray tracing is forward ray tracing in which rays are traced from the object toward the image plane.

In general, a spherical lens system comprising only a spherical lens is arranged such that aberrations produced by spherical surfaces, such as spherical aberration, coma and curvature of field, are corrected with some surfaces by canceling the aberrations with each other, thereby reducing aberrations as a whole.

On the other hand, rotationally symmetric aspherical surfaces and the like are used to correct aberrations favorably with a minimal number of surfaces. The reason for this is to reduce various aberrations that would be produced by spherical surfaces.

However, in a decentered optical system, rotationally asymmetric aberrations due to decentration cannot be corrected by a rotationally symmetric optical system. Rotationally asymmetric aberrations due to decentration include distortion, curvature of field, and astigmatic and comatic aberrations, which occur even on the axis.

First, rotationally asymmetric curvature of field will be described. For example, when rays from an infinitely distant object point are incident on a decentered concave mirror, the rays are reflected by the concave mirror to form an image. In this case, the back focal length from that portion of the concave mirror on which the rays strike to the image surface is a half the radius of curvature of the portion on which the rays strike in a case where the medium on the image side is air. Consequently, as shown in FIG. 17, an image surface tilted with respect to the axial principal ray is formed. It is impossible to correct such rotationally asymmetric curvature of field by a rotationally symmetric optical system.

To correct the tilted curvature of field by the concave mirror M itself, which is the source of the curvature of field, the concave mirror M is formed from a rotationally asymmetric surface, and, in this example, the concave mirror M is arranged such that the curvature is made strong (refracting power is increased) in the positive direction of the Y-axis, whereas the curvature is made weak (refracting power is reduced) in the negative direction of the Y-axis. By doing so, the tilted curvature of field can be corrected. It is also possible to obtain a flat image surface with a minimal number of constituent surfaces by placing a rotationally asymmetric surface having the same effect as that of the above-described arrangement in the optical system separately from the concave mirror M.

It is preferable that the rotationally asymmetric surface should be a rotationally asymmetric surface having no axis of rotational symmetry in the surface nor out of the surface. If the rotationally asymmetric surface has no axis of rotational symmetry in the surface nor out of the surface, the degree of freedom increases, and this is favorable for aberration correction.

Next, rotationally asymmetric astigmatism will be described.

A decentered concave mirror M produces astigmatism even for axial rays, as shown in FIG. 18, as in the case of the above. The astigmatism can be corrected by appropriately changing the curvatures in the X- and Y-axis directions of the rotationally asymmetric surface as in the case of the above.

Rotationally asymmetric coma will be described below.

A decentered concave mirror M produces coma even for axial rays, as shown in FIG. 19, as in the case of the above. The coma can be corrected by changing the tilt of the rotationally asymmetric surface according as the distance from the origin of the X-axis increases, and further appropriately changing the tilt of the surface according to the sign (positive or negative) of the Y-axis.

The image-forming optical system according to the present invention may also be arranged such that the above-described at least one surface having a reflecting action is decentered with respect to the axial principal ray and has a rotationally asymmetric surface configuration and further has a power. By adopting such an arrangement, decentration aberrations produced as the result of giving a power to the reflecting surface can be corrected by the surface itself. In addition, the power of the refracting surfaces of the prism is reduced, and thus chromatic aberration produced in the prism can be minimized.

The rotationally asymmetric surface used in the present invention should preferably be a plane-symmetry free-form surface having only one plane of symmetry. Free-form surfaces used in the present invention are defined by the following equation (a). It should be noted that the Z-axis of the defining equation is the axis of a free-form surface.

$$Z = cr^2 / \left[1 + \sqrt{\{1 - (1+k)c^2 r^2\}}\right] + \sum_{j=2}^{66} C_j X^m Y^n \quad (a)$$

In Eq. (a), the first term is a spherical surface term, and the second term is a free-form surface term.

In the spherical surface term:

c: the curvature at the vertex k: a conic constant $r = \sqrt{(X^2 + Y^2)}$

The free-form surface term is given by $$\sum_{j=2}^{66} C_j X^m Y^n = C_2 X + C_3 Y + C_4 X^2 + C_5 XY + C_6 Y^2 + C_7 X^3 +$$

$$C_8 X^2 Y + C_9 XY^2 + C_{10} Y^3 + C_{11} X^4 + C_{12} X^3 Y +$$

$$C_{14} XY^3 + C_{15} Y^4 + C_{16} X^5 + C_{17} X^4 Y + C_{18} X^3 Y^2 +$$

$$C_{19} X^2 Y^3 + C_{20} XY^4 + C_{21} Y^5 + C_{22} X^6 + C_{23} X^5 Y +$$

$$C_{24} X^4 Y^2 + C_{25} X^3 Y^3 + C_{26} X^2 Y^4 + C_{27} XY^5 +$$

$$C_{28} Y^6 + C_{29} X^7 + C_{30} X^6 Y + C_{31} X^5 Y^2 +$$

$$C_{32} X^4 Y^3 + C_{33} X^3 Y^4 + C_{34} X^2 Y^5 + C_{35} XY^6 +$$

$$C_{36} Y^7$$

where $C_j$ (j is an integer of 2 or higher) are coefficients.

In general, the above-described free-form surface does not have planes of symmetry in both the XZ- and YZ-planes. In the present invention, however, a free-form surface having only one plane of symmetry parallel to the YZ-plane is obtained by making all terms of odd-numbered degrees with respect to X zero. For example, in the above defining equation (a), the coefficients of the terms $C_2$, $C_5$, $C_7$, $C_9$, $C_{12}$, $C_{14}$, $C_{16}$, $C_{18}$, $C_{20}$, $C_{23}$, $C_{25}$, $C_{27}$, $C_{29}$, $C_{31}$, $C_{33}$, $C_{35}$, . . . are set equal to zero. By doing so, it is possible to obtain a free-form surface having only one plane of symmetry parallel to the YZ-plane.

A free-form surface having only one plane of symmetry parallel to the XZ-plane is obtained by making all terms of odd-numbered degrees with respect to Y zero. For example, in the above defining equation (a), the coefficients of the terms $C_3$, $C_5$, $C_8$, $C_{10}$, $C_{12}$, $C_{14}$, $C_{17}$, $C_{19}$, $C_{21}$, $C_{23}$, $C_{25}$, $C_{27}$, $C_{30}$, $C_{32}$, $C_{34}$, $C_{36}$ . . . are set equal to zero. By doing so, it is possible to obtain a free-form surface having only one plane of symmetry parallel to the XZ-plane.

Furthermore, the direction of decentration is determined in correspondence to either of the directions of the above-described planes of symmetry. For example, with respect to the plane of symmetry parallel to the YZ-plane, the direction of decentration of the optical system is determined to be the Y-axis direction. With respect to the plane of symmetry parallel to the XZ-plane, the direction of decentration of the optical system is determined to be the X-axis direction. By doing so, rotationally asymmetric aberrations due to decentration can be corrected effectively, and at the same time, productivity can be improved.

It should be noted that the above defining equation (a) is shown as merely an example, and that the feature of the present invention resides in that rotationally asymmetric aberrations due to decentration are corrected and, at the same time, productivity is improved by using a rotationally asymmetric surface having only one plane of symmetry. Therefore, the same advantageous effect can be obtained for any other defining equation that expresses such a rotationally asymmetric surface.

In the present invention, the prism object-side part and the prism image-side part may be made of different materials and cemented together. Alternatively, the prism object-side part and the prism image-side part may be placed adjacently to each other with a small spacing therebetween. In either case, the advantageous effects of the present invention can be obtained satisfactorily.

Incidentally, it is desirable to arrange the prism optical system such that the reflecting surface B and the transmitting surface A, which are placed in the image-side part of the prism optical system, are positioned to face each other across the prism medium, and the surface C, which reflects a light beam from the prism object-side part, is disposed between the surfaces B and A so that an optical path connecting the surfaces B and A intersects an optical path connecting the prism object-side part and the surface C.

The prism having the above-described configuration enables an increase in the degree of freedom for aberration correction and produces minimal aberrations. In addition, because the two reflecting surfaces in the prism image-side part can be positioned with a high degree of symmetry, aberrations produced by the two reflecting surfaces are corrected with these reflecting surfaces by canceling the aberrations each other. Therefore, the amount of aberration produced in the prism is favorably small. Furthermore, because the above-described two optical paths are arranged to intersect each other in the prism image-side part, the optical path length can be made long in comparison to a prism structure in which the optical path is simply folded. Accordingly, the prism can be made compact in size, considering its optical path length. It is more desirable that the two reflecting surfaces in the prism image-side part should have powers of different signs. By doing so, it is possible to enhance the effect of correcting each other's aberrations by the two reflecting surfaces and hence possible to obtain high resolution.

In addition, if the prism image-side part is formed by using a prism structure in which the optical paths intersect each other as stated above, it is possible to construct the prism image-side part in a compact form. The reason for this is as follows. In a comparison between the prism structure used in the present invention and a prism structure of the same two-reflection type which has the same optical path length as that of the above-described prism structure and in which a Z-shaped optical path is formed, the prism structure used in the present invention provides a higher space utilization efficiency. In the prism having a Z-shaped optical path, rays invariably travel through different regions of the prism one by one, whereas in the prism in which the optical paths intersect each other, rays pass through the same region twice. Accordingly, the prism can be made compact in size.

Furthermore, both the surfaces C and B of the prism image-side part may be arranged to have a rotationally asymmetric surface configuration that gives a power to a light beam and corrects aberrations due to decentration.

Furthermore, the rotationally asymmetric surface configuration of at least one of the surfaces C and B in the prism image-side part may be arranged in the form of a plane-symmetry free-form surface having only one plane of symmetry.

When both the surfaces C and B of the prism image-side part have rotationally asymmetric surface configurations, the rotationally asymmetric surface configuration of each of the two surfaces may be arranged in the form of a plane-symmetry free-form surface having only one plane of symmetry.

In this case, the prism image-side part may be arranged such that the only one plane of symmetry of the plane-symmetry free-form surface that forms the surface C and the only one plane of symmetry of the plane-symmetry free-form surface that forms the surface B are formed in the same plane.

The surface A of the prism image-side part may have a rotationally asymmetric surface configuration that gives a power to a light beam and corrects aberrations due to decentration. A refracting surface having such a surface configuration is effective in correcting aberrations due to decentration.

In this case, the rotationally asymmetric surface configuration of the surface A of the prism image-side part may be arranged in the form of a plane-symmetry free-form surface having only one plane of symmetry.

Furthermore, a rotationally asymmetric surface placed in the prism object-side part may be arranged in the form of a plane-symmetry free-form surface having only one plane of symmetry.

The arrangement may be such that the prism object-side part and the prism image-side part each have at least one plane-symmetry free-form surface having only one plane of symmetry, and the only one plane of symmetry of the at least one plane-symmetry free-form surface in the prism object-side part and that of the at least one plane-symmetry free-form surface in the prism image-side part are placed in the same plane.

By using a reflecting surface having a negative refracting power to form the prism object-side part, a wide field angle for imaging can be obtained. This is because the negative power enables rays of wide field angle to be converged and thus it is possible to converge the light beam when the rays are incident on a reflecting surface provided in the prism image-side part. This is favorable from the viewpoint of aberration correction when an optical system having a relatively short focal length is to be constructed.

In the present invention, the effective way of enhancing the symmetry required for the image-forming optical system and thereby favorably correcting aberrations, including off-axis aberrations, is to place a pupil between the prism object-side part and the prism image-side part and to place the prism image-side part between the pupil and the image plane.

In this case, a stop can be placed on the pupil (particularly, in a case where the prism object-side part and the prism image-side part are cemented together, or they are placed adjacently to each other with a small spacing therebetween).

In the present invention, the prism object-side part, exclusive of the surfaces A, B and C, may be arranged to have two or more reflecting surfaces with a curved surface configuration that gives a power to a light beam.

In this case, the prism object-side part, exclusive of the surfaces A, B and C, may be formed from two optical surfaces, i.e. an entrance surface serving as both a reflecting surface and a transmitting surface, and a reflecting surface. In other words, the second reflecting surface and the first transmitting surface may be formed from a single surface serving as both reflecting and transmitting surfaces. With this arrangement, the first reflecting surface reflects incident rays toward the second reflecting surface at a minimal angle of deviation, and the second reflecting surface bends the rays to a considerable extent. Therefore, it is possible to reduce the thickness of the prism in the direction of the incident rays.

In a case where the prism object-side part is arranged as stated above, it is preferable to give a negative power to the first reflecting surface (a positive power may be locally present in the first reflecting surface). By doing so, it is possible to lengthen the optical path length along an optical path between the first reflecting surface and a surface having a positive power in the prism image-side part. Consequently, the positive and negative powers of the two surfaces can be weakened, and it becomes possible to minimize aberrations produced by these surfaces. Thus, it is possible to maintain the required aberration correcting performance and to widen the field angle most effectively.

It is preferable to place the stop on the image side of the prism object-side part. By doing so, in a case where the first reflecting surface has a negative power and is approximated by a spherical surface, the center of curvature of the first reflecting surface and the stop position are approximately coincident with each other. Therefore, it is possible to eliminate comatic aberration in theory.

In the present invention, the prism object-side part, exclusive of the surfaces A, B and C, may comprise an entrance surface having a transmitting action by which a light beam is allowed to enter the prism, and two reflecting surfaces that give a power to a light beam.

In this case, it is particularly desirable to arrange the prism object-side part such that the two reflecting surfaces face each other across the prism medium, and the entrance surface and the two reflecting surfaces form a Z-shaped optical path.

The above-described prism configuration enables an increase in the degree of freedom for aberration correction and produces minimal aberrations. In addition, because the relative decentration between the two reflecting surfaces is small, aberrations produced by the two reflecting surfaces are corrected with these reflecting surfaces by canceling the aberrations each other. Therefore, the amount of aberration produced in the prism is favorably small. It is more desirable that the two reflecting surfaces should have powers of different signs. By doing so, it is possible to enhance the effect of correcting each other's aberrations by the two reflecting surfaces and hence possible to obtain high resolution.

It is even more desirable to give a negative power to the first reflecting surface. By doing so, it is possible to lengthen the optical path length along an optical path between the first reflecting surface and a surface having a positive power in the prism image-side part. Consequently, the positive and negative powers of the two surfaces can be weakened, and it becomes possible to minimize aberrations produced by these surfaces. It is also preferable to place the stop on the image side of the prism object-side part. By doing so, in a case where the first reflecting surface has a negative power and is approximated by a spherical surface, the center of curvature of the first reflecting surface and the stop position are approximately coincident with each other. Therefore, it is possible to eliminate comatic aberration in theory.

In the present invention, the prism object-side part, exclusive of the surfaces A, B and C, may be formed from three optical surfaces, i.e. an entrance surface serving as both a reflecting surface and a transmitting surface, and two reflecting surfaces.

In this type of prism, the first transmitting Surface and the second reflecting surface are formed from a single surface serving as both transmitting and reflecting surfaces. The first reflecting surface reflects incident rays toward the second reflecting surface at a minimal angle of deviation. The second reflecting surface bends rays to a considerable extent. The third reflecting surface bends rays at a minimal angle of deviation. Therefore, it is possible to reduce the thickness of the prism in the direction of the incident rays. In addition, in a case where a stop is placed between the prism object-side part and the prism image-side part, it is possible to lengthen the optical path length from the stop position to the first reflecting surface, which usually has a strong negative refracting power, in the prism. Accordingly, a thin optical system can be constructed. Moreover, the distance between the prism object-side part and the prism image-side part can be shortened.

By arranging the prism object-side part to have a negative refracting power, a wide field angle for imaging can be obtained. This is because the negative power enables rays of wide field angle to be converged and thus it is possible to converge the light beam when the rays are incident on the second unit, which comprises the prism image-side part. This is favorable from the viewpoint of aberration correction when an optical system having a relatively short focal length is to be constructed.

When a prism object-side part having the above-described arrangement is used, it is preferable for the second reflecting surface to effect the reflection in the prism by a totally reflecting action so as to serve as both transmitting and reflecting surfaces.

In addition, it is preferable for the first reflecting surface of the prism object-side part to have a reflecting surface configuration that gives a negative power to a light beam reflected in the prism as a whole (a positive power may be locally present in the first reflecting surface).

By virtue of the above-described arrangement, it is possible to lengthen the optical path length along an optical path between the first reflecting surface and a surface having a positive power in the prism image-side part. Consequently, the positive and negative powers of the two surfaces can be weakened, and it becomes possible to minimize aberrations produced by these surfaces. Thus, it is possible to maintain the required aberration correcting performance and to widen the field angle most effectively.

In the prism of the present invention, reflecting surfaces other than a totally reflecting surface are preferably formed from a reflecting surface having a thin film of a metal, e.g. aluminum or silver, formed on the surface thereof, or a reflecting surface formed from a dielectric multilayer film. In the case of a metal thin film having reflecting action, a high reflectivity can be readily obtained. The use of a dielectric reflecting film is advantageous in a case where a reflecting film having wave-length selectivity or minimal absorption is to be formed.

Thus, it is possible to obtain a low-cost and compact image-forming optical system in which the prism manufacturing accuracy is favorably eased.

In the present invention, it is desirable for the image-forming optical system to have a prism object-side part having a diverging action on the object side of a stop and a prism image-side part having a converging action on the image side of the stop, and also desirable for the image-forming optical system to be approximately telecentric on the image side.

In an image-forming optical system using a refracting optical element, the power distribution varies according to the use application. For example, telephoto systems having a narrow field angle generally adopt an arrangement in which the entire system is formed as a telephoto type having a positive front unit and a negative rear unit, thereby making the overall length of the optical system shorter than the focal length. Wide-angle systems having a wide field angle generally adopt an arrangement in which the entire system is formed as a retrofocus type having a negative front unit and a positive rear unit, thereby making the back focus longer than the focal length.

In the case of an image-forming optical system using an image pickup device, e.g. a CCD, in particular, it is necessary to place an optical low-pass filter, an infrared cutoff filter, etc. between the image-forming optical system and the image pickup device to remove moire and to eliminate the influence of infrared rays. Therefore, with a view to ensuring a space for placing these optical members, it is desirable to adopt a retrofocus type arrangement for the image-forming optical system.

It is important for a retrofocus type image-forming optical system to be corrected for aberrations, particularly off-axis aberrations. The correction of off-axis aberrations depends largely on the position of the stop. As has been stated above, in the case of a general coaxial optical system, off-axis aberrations are aggravated if optical elements are not in symmetry with respect to the stop. For this reason, the common practice is to place optical elements of the same sign at respective positions facing each other across the stop, thereby obtaining a satisfactory symmetry with respect to the stop, and thus correcting off-axis aberrations. In the case of a retrofocus type system having a negative front unit and a positive rear unit, the power distribution is asymmetric in the first place. Therefore, the off-axis aberration-correcting performance varies to a considerable extent according to the position of the stop.

Therefore, the stop is placed between the prism object-side part having a diverging action and the prism image-side part having a converging action, thereby making it possible to minimize the aggravation of off-axis aberrations due to the asymmetry of the power distribution. If the-stop is placed on the object side of the prism object-side part having a diverging action or on the image side of the prism image-side part having a converging action, the asymmetry with respect to the stop is enhanced and becomes difficult to correct.

In this case, the image-forming optical system may consist of a prism in which the prism object-side part of diverging action is placed on the object side of the stop, and the prism image-side part of converging action is placed on the image side of the stop.

In the image-forming optical systems according to the present invention, there is only one image-formation plane throughout the system. As has been stated above, the decentration error sensitivity of a reflecting surface is higher than that of a refracting surface. In a reflecting optical member arranged in the form of a single block as in the case of a prism, surface accuracy errors and decentration errors of each surface are transferred while being added up. Therefore, the smaller the number of reflecting surfaces, the more the manufacturing accuracy required for each surface is eased. Accordingly, it is undesirable to increase the number of reflections more than is needed. For example, in an image-forming optical system in which an intermediate image is formed and this image is relayed, the number of reflections increases more than is needed, and the manufacturing accuracy required for each surface becomes tight, causing the cost to increase unfavorably.

Let us define the power of a decentered optical system and that of a decentered optical surface. As shown in FIG. 20, when the direction of decentration of a decentered optical system S is taken in the Y-axis direction, a light ray which is parallel to the axial principal ray of the decentered optical system S and which has a small height d in the YZ-plane is made to enter the decentered optical system S from the object side thereof. The angle that is formed between that ray and the axial principal ray exiting from the decentered optical system S as the two rays are projected onto the YZ-plane is denoted by δy, and δy/d is defined as the power Py in the Y-axis direction of the decentered optical system S. Similarly, a light ray which is parallel to the axial principal ray of the decentered optical system S and which has a small height d in the X-axis direction, which is perpendicular to the YZ-plane, is made to enter the decentered optical system S from the object side thereof. The angle that is formed between that ray and the axial principal ray exiting from the decentered optical system S as the two rays are projected onto a plane perpendicularly intersecting the YZ-plane and containing the axial principal ray is denoted by δx, and δx/d is defined as the power Px in the X-axis direction of the decentered optical system S. The power Pyn in the Y-axis direction and power Pxn in the X-axis direction of a decentered optical surface n constituting the decentered optical system S are defined in the same way as the above.

Furthermore, the reciprocals of the above-described powers are defined as the focal length Fy in the Y-axis direction of the decentered optical system S, the focal length Fx in the X-axis direction of the decentered optical system S, the focal length Fyn in the Y-axis direction of the decentered optical surface n, and the focal length Fxn in the X-axis direction of the decentered optical surface n, respectively.

When the powers in the X- and Y-axis directions of the surface B having a reflecting action are denoted by Pxb and Pyb, respectively, and the powers in the X- and Y-axis directions of the prism are denoted by Px and Py, respectively, it is preferable to satisfy the following condition:

$$0 < Pxb/Px < 2 \tag{1}$$

The condition (1) limits the power of the surface B having a reflecting action in the prism image-side part. The surface B needs to have a relatively strong power in the whole optical system. The surface B is characterized in that because it has a relatively small amount of decentration with respect to rays, even if the surface B has a strong power, it produces a relatively small amount of decentration aberrations.

If Pxb/Px is not larger than the lower limit of the condition (1), i.e. 0, the surface B has no power. Consequently, another surface needs to have a strong power, and the amount of decentration aberrations produced by this surface becomes unfavorably large. If Pxb/Px is not smaller-than the upper limit of the condition (1), i.e. 2, the power of the surface B becomes excessively strong, and the amount of decentration aberrations produced by the surface B becomes unfavorably large.

It is even more desirable to satisfy the following condition:

$$0 < Pxb/Px < 0.8 \tag{1-1}$$

It is still more desirable to satisfy the following condition:

$$0.2 < Pxb/Px < 0.6 \tag{1-2}$$

It is also preferable to satisfy the following condition:

$$-0.5 < Pyb/Py < 2 \tag{2}$$

The meaning of the condition (2) is the same as that of the condition (1). Therefore, a description thereof is omitted.

It is even more desirable to satisfy the following condition:

$$0 < Pyb/Py < 1 \tag{2-1}$$

It is still more desirable to satisfy the following condition:

$$0 < Pyb/Py < 0.6 \tag{2-2}$$

When the powers in the X- and Y-axis directions of the surface C having a reflecting action are denoted by Pxc and Pyc, respectively, and the powers in the X- and Y-axis directions of the prism are denoted by Px and Py, respectively, it is preferable to satisfy the following condition:

$$0 < Pxc/Px < 2 \tag{3}$$

The condition (3) limits the power of the surface C having a reflecting action in the prism image-side part. The surface C needs to have a relatively strong power in the whole optical system. The surface C is characterized in that because it has a relatively small amount of decentration with respect to rays, even if the surface C has a strong power, it produces a relatively small amount of decentration aberrations.

If Pxc/Px is not larger than the lower limit of the condition (3), i.e. 0, the surface C has no power. Consequently, another surface needs to have a strong power, and the amount of decentration aberrations produced by this surface becomes unfavorably large. If Pxc/Px is not smaller than the upper limit of the condition (3), i.e. 2, the power of the surface C becomes excessively strong, and the amount of decentration aberrations produced by the surface C becomes unfavorably large.

It is even more desirable to satisfy the following condition:

$$0 < Pxc/Px < 1 \tag{3-1}$$

It is still more desirable to satisfy the following condition:

$$0.2 < Pxc/Px < 0.6 \tag{3-2}$$

It is also preferable to satisfy the following condition:

$$0 < Pyc/Py < 2 \tag{4}$$

The meaning of the condition (4) is the same as that of the condition (3). Therefore, a description thereof is omitted.

It is even more desirable to satisfy the following condition:

$$0 < Pyc/Py < 1 \quad (4\text{-}1)$$

It is still more desirable to satisfy the following condition:

$$0 < Pyc/Py < 0.4 \quad (4\text{-}2)$$

Next, when the incident angles of the axial principal ray on the surfaces B and C are denoted by $\alpha b$ and $\alpha c$, respectively, it is preferable to satisfy the following condition:

$$5° < \alpha b < 45° \quad (5)$$

The condition (5) relates to the power of the surface B. In the present invention, the condition (5) is a condition for placing the surfaces C and B adjacently to each other and making the optical paths intersect each other. If $\alpha b$ is not larger than the lower limit of the condition (5), i.e. 5°, the lengths of the intersecting optical paths become unfavorably long, and it becomes impossible to construct the optical system in a compact form. If $\alpha b$ is not smaller than the upper limit of the condition (5), i.e. 45°, it becomes impossible to realize an arrangement in which the optical paths intersect each other.

It is even more desirable to satisfy the following condition:

$$10° < \alpha b < 40° \quad (5\text{-}1)$$

If $\alpha b$ is not smaller than the upper limit of the condition (5-1), i.e. 40°, in particular, the amount of decentration of the surface B becomes excessively large. Consequently, decentration aberrations produced by the surface B become excessively large and hence impossible to correct by another surface.

It is still more desirable to satisfy the following conditions:

$$20° < \alpha b < 30° \quad (5\text{-}2)$$

It is also preferable to satisfy the following condition:

$$5° < \alpha c < 45° \quad (6)$$

The condition (6) relates to the power of the surface C. In the present invention, the condition (6) is a condition for placing the surfaces C and B adjacently to each other and making the optical paths intersect each other. If $\alpha c$ is not larger than the lower limit of the condition (6), i.e. 5°, the lengths of the intersecting optical paths become unfavorably long, and it becomes impossible to construct the optical system in a compact form. If $\alpha c$ is not smaller than the upper limit of the condition (6), i.e. 45°, it becomes impossible to realize an arrangement in which the optical paths intersect each other.

It is even more desirable to satisfy the following condition:

$$10° < \alpha c < 40° \quad (6\text{-}1)$$

If $\alpha c$ is not smaller than the upper limit of the condition (6-1), i.e. 40°, in particular, the amount of decentration of the surface C becomes excessively large. Consequently, decentration aberrations produced by the surface C become excessively large and hence impossible to correct by another surface.

It is still more desirable to satisfy the following conditions:

$$20° < \alpha c < 30° \quad (6\text{-}2)$$

Next, when the ratio of $\alpha c$ to $\alpha b$, i.e. $\alpha c/\alpha b$, is denoted by $\alpha bc$, it is preferable to satisfy the following condition:

$$0.2 < \alpha bc < 3 \quad (7)$$

The condition (7) is a condition for a portion of the prism image-side part that forms the intersecting optical paths. It is important that the surface B and the surface C should be decentered with good balance. If $\alpha bc$ is not larger than the lower limit of the condition (7), i.e. 0.2, the incident angle on the surface B becomes excessively larger than the incident angle on the surface C. Consequently, the amount of decentration aberrations produced by the surface B becomes excessively large. If $\alpha bc$ is not smaller than the upper limit of the condition (7), i.e. 3, the incident angle on the surface C becomes excessively larger than the incident angle on the surface B. Consequently, the amount of decentration aberrations produced by the surface C becomes excessively large.

It is even more desirable to satisfy the following condition:

$$0.4 < \alpha bc < 2 \quad (7\text{-}1)$$

It is still more desirable to satisfy the following condition:

$$0.6 < \alpha bc < 1.2 \quad (7\text{-}2)$$

Next, in a case where the prism object-side part has at least two reflecting surfaces, when the powers in the X- and Y-axis directions of the first reflecting surface are denoted by Px1 and Py1, respectively, and the powers in the X- and Y-axis directions of the prism are denoted by Px and Py, respectively, it is preferable to satisfy the following condition:

$$-5 < Px1/Px < 0 \quad (8)$$

If Px1/Px is not larger than the lower limit of the condition (8), i.e. −5, the negative power of the first reflecting surface becomes excessively strong. Consequently, decentration aberrations, particularly image distortion due to decentration, produced by this surface become large and hence difficult to correct by another surface. If Px1/Px is not smaller than the upper limit of the condition (8), i.e. 0, a retrofocus type optical system cannot be realized, and it becomes difficult to ensure a wide field angle for observation.

To ensure a horizontal half field angle of 15° or more, in particular, it is even more desirable to satisfy the following condition:

$$-2 < Px1/Px < -0.3 \quad (8\text{-}1)$$

It is also preferable to satisfy the following condition:

$$-4 < Py1/Py < 0 \quad (9)$$

If Py1/Py is not larger than the lower limit of the condition (9), i.e. −4, the negative power of the first reflecting surface becomes excessively strong. Consequently, decentration aberrations, particularly image distortion due to decentration, produced by this surface become large and hence difficult to correct by another surface. If Py1/Py is not smaller than the upper limit of the condition (9), i.e. 0, a retrofocus type optical system cannot be realized, and it becomes difficult to ensure a wide field angle for observation.

To ensure a horizontal half field angle of 15° or more, in particular, it is even more desirable to satisfy the following condition:

$$-2 < Py1/Py < -0.1 \quad (9\text{-}1)$$

When the powers in the X- and Y-axis directions of the second reflecting surface are denoted by Px2 and Py2, respectively, and the powers in the X- and Y-axis directions of the prism are denoted by Px and Py, respectively, it is preferable to satisfy the following condition:

$$-2 < Px2/Px < 4 \quad (10)$$

The condition (10) is a condition for the second reflecting surface. The second reflecting surface reflects rays at a large angle to lead them to the image plane. Accordingly, the angle at which rays are incident on the second reflecting surface is large. If Px2/Px is not larger than the lower limit of the condition (10), i.e. −2, or not smaller than the upper limit, i.e. 4, the second reflecting surface has an excessively strong power. Consequently, decentration aberrations produced by this surface become excessively large and hence impossible to correct by another surface. Because the second reflecting surface is relatively close to the stop position, decentration aberrations, particularly coma due to decentration, produced by this surface become large and hence difficult to correct by another surface.

It is even more desirable to satisfy the following condition:

$$-1 < Px2/Px < 2 \quad (10\text{-}1)$$

It is still more desirable to satisfy the following condition:

$$0 < Px2/Px < 1 \quad (10\text{-}2)$$

It is also preferable to satisfy the following condition:

$$-2 < Py2/Py < 2 \quad (11)$$

The condition (11) is also a condition for the second reflecting surface. The second reflecting surface reflects rays at a large angle to lead them to the image plane. Accordingly, the angle at which rays are incident on the second reflecting surface is large. If Py2/Py is not larger than the lower limit of the condition (11), i.e. −2, or not smaller than the upper limit, i.e. 2, the second reflecting surface has an excessively strong power. Consequently, decentration aberrations produced by this surface become excessively large and hence impossible to correct by another surface. Because the second reflecting surface is relatively close to the stop position, decentration aberrations, particularly coma due to decentration, produced by this surface become large and hence difficult to correct by another surface.

It is even more desirable to satisfy the following condition:

$$-1 < Py2/Py < 0.8 \quad (11\text{-}1)$$

It is still more desirable to satisfy the following condition:

$$-0.5 < Py2/Py < 0.5 \quad (11\text{-}2)$$

In the image-forming optical system according to the present invention, focusing of the image-forming optical system can be effected by moving all the constituent elements or moving the prism. However, it is also possible to effect focusing by moving the image-formation plane in the direction of the axial principal ray exiting from the surface closest to the image side. By doing so, it is possible to prevent displacement of the axial principal ray on the entrance side due to focusing even if the direction in which the axial principal ray from the object enters the optical system is not coincident with the direction of the axial principal ray exiting from the surface closest to the image side owing to the decentration of the image-forming optical system. It is also possible to effect focusing by moving a plurality of wedge-shaped prisms, which are formed by dividing a plane-parallel plate, in a direction perpendicular to the Z-axis. In this case also, focusing can be performed independently of the decentration of the image-forming optical system.

In the present invention, temperature compensation can be made by forming the prism object-side part and the prism image-side part using different materials. By providing the prism object-side part and the prism image-side part with powers of different signs, it is possible to prevent the focal shift due to changes in temperature, which is a problem arising when a plastic material is used to form a prism.

In a case where the two prism parts of the present invention are cemented together, it is desirable that each of the two prism parts should have a positioning portion for setting a relative position on a surface having no optical action. In a case where two prism parts each having a reflecting surface with a power are cemented together as in the present invention, in particular, relative displacement of each prism part causes the performance to be deteriorated. Therefore, in the present invention, a positioning portion for setting a relative position is provided on each surface of each prism part that has no optical action, thereby ensuring the required positional accuracy. Thus, the desired performance can be ensured. In particular, if the two prism parts are integrated into one unit by using the positioning portions and coupling members, it becomes unnecessary to perform assembly adjustment. Accordingly, the cost can be further reduced.

Furthermore, the optical path can be folded in a direction different from the decentration direction of the image-forming optical system according to the present invention by placing a reflecting optical member, e.g. a mirror, on the object side of the entrance surface of the image-forming optical system. By doing so, the degree of freedom for layout of the image-forming optical system further increases, and the overall size of the image-forming optical apparatus can be further reduced.

In the present invention, the image-forming optical system can be formed from a prism alone. By doing so, the number of components is reduced, and the cost is lowered. Furthermore, two prisms may be integrated into one prism with a stop put therebetween. By doing so, the cost can be further reduced.

In the present invention, the image-forming optical system may include another lens (positive or negative lens) as a constituent element in addition to the prism at either or each of the object and image sides of the prism.

The image-forming optical system according to the present invention may be a fast, single focal length lens system. Alternatively, the image-forming optical system may be arranged in the form of a zoom lens system (variable-magnification image-forming optical system) by combining it with a single or plurality of refracting optical systems that may be provided on the object or image side of the prism.

In the present invention, the refracting and reflecting surfaces of the image-forming optical system may be formed from spherical surfaces or rotationally symmetric aspherical surfaces.

In a case where the above-described image-forming optical system according to the present invention is placed in an image pickup part of an image pickup apparatus, or in a case where the image pickup apparatus is a photographic apparatus having a camera mechanism, it is possible to adopt an arrangement in which a prism member is placed closest to the object side among optical elements having an optical action, and the entrance surface of the prism member is decentered with respect to the optical axis, and further a cover member is placed on the object side of the prism member at right angles to the optical axis. The arrangement may also be such that the prism member has on the object side thereof an entrance surface decentered with respect to the optical axis, and a cover lens having a power is placed on the object side of the entrance surface of the prism member in coaxial relation to the optical axis so as to face the entrance surface across an air spacing.

If a prism member is placed closest to the object side and a decentered entrance surface is provided on the front side of a photographic apparatus as stated above, the obliquely tilted entrance surface is seen from the subject, and it gives the illusion that the photographic center of the apparatus is deviated from the subject when the entrance surface is seen from the subject side. Therefore, a cover member or a cover lens is placed at right angles to the optical axis, thereby preventing the subject from feeling incongruous when seeing the entrance surface, and allowing the subject to be photographed with the same feeling as in the case of general photographic apparatus.

A finder optical system can be formed by using any of the above-described image-forming optical systems according to the present invention as a finder objective optical system and adding an image-inverting optical system for erecting an object image formed by the finder objective optical system and an ocular optical system.

In addition, it is possible to construct a camera apparatus by using the finder optical system and an objective optical system for photography provided in parallel to the finder optical system.

In addition, an image pickup optical system can be constructed by using any of the foregoing image-forming optical systems according to the present invention and an image pickup device placed in an image plane formed by the image-forming optical system.

In addition, a camera apparatus can be constructed by using any of the foregoing image-forming optical systems according to the present invention as an objective optical system for photography, and a finder optical system placed in an optical path separate from an optical path of the objective optical system for photography or in an optical path split from the optical path of the objective optical system for photography.

In addition, an electronic camera apparatus can be constructed by using any of the foregoing image-forming optical systems according to the present invention, an image pickup device placed in an image plane formed by the image-forming optical system, a recording medium for recording image information received by the image pickup device, and an image display device that receives image information from the recording medium or the image pickup device to form an image for observation.

In addition, an endoscope system can be constructed by using an observation system having any of the foregoing image-forming optical systems according to the present invention and an image transmitting member for transmitting an image formed by the image-forming optical system along a longitudinal axis, and an illumination system having an illuminating light source and an illuminating light transmitting member for transmitting illuminating light from the illuminating light source along the longitudinal axis.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

Examples 1 to 15 of the image-forming optical system according to the present invention will be described below. It should be noted that constituent parameters of each example will be shown later.

Figure 1:
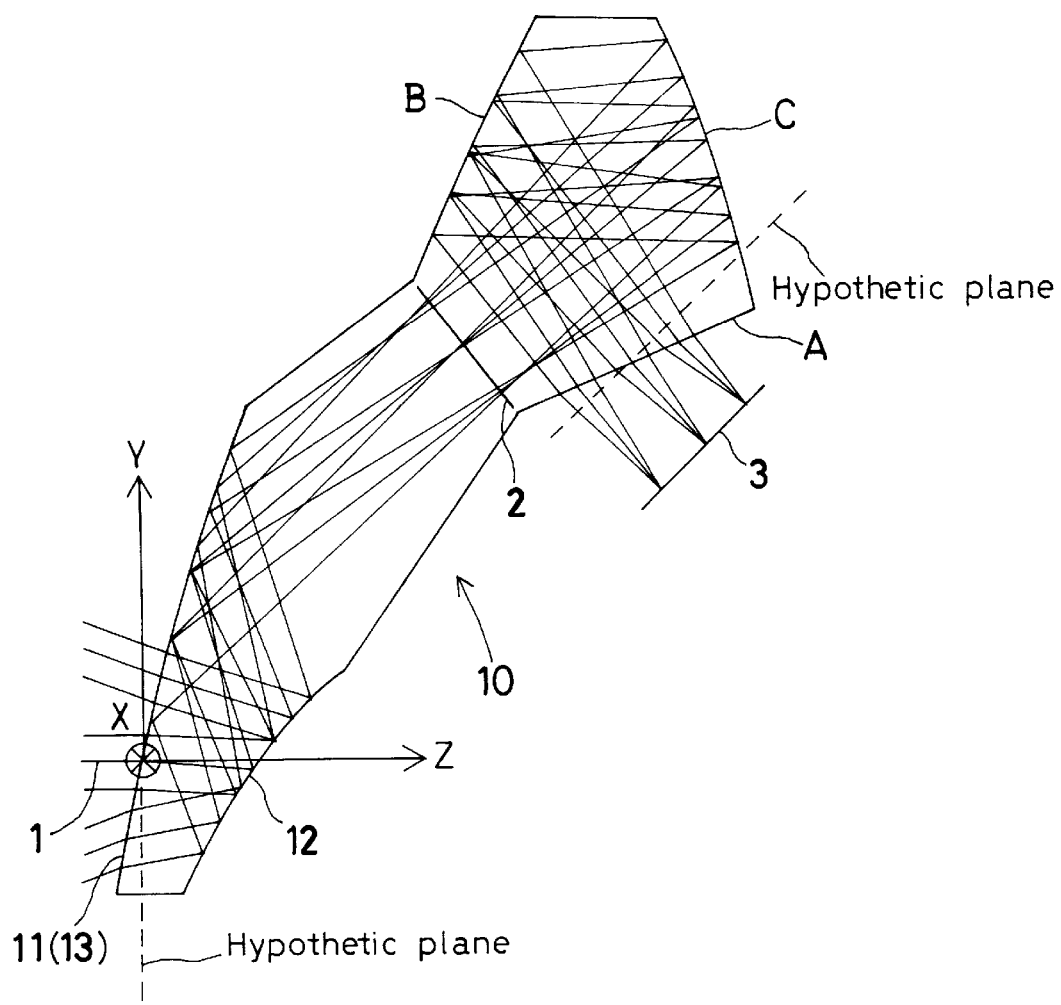
FIG. 1 is a sectional view of an image-forming optical system according to Example 1 of the present invention.

In each example, as shown in FIG. 1, an axial principal ray 1 is defined by a ray emanating from the center of an object and passing through the center of a stop 2 to reach the center of an image plane 3. A hypothetic plane is taken in a plane extending through the intersection between the axial principal ray 1 and an entrance surface (first surface) 11 of a prism 10 at right angles to the axial principal ray 1 entering the entrance surface 11. Another hypothetic plane is taken in a plane extending through the intersection between the axial principal ray 1 and an exit surface (surface A) A of the prism 10 at right angles to the axial principal ray 1 exiting from the exit surface A. Further, a reference plane is taken in a stop (pupil) plane 2. The intersection of each hypothetic plane and the associated optical surface and the intersection between the axial principal ray 1 and the stop plane 2 are each defined as the origin for decentered optical surfaces present between the optical surface and the stop plane 2 or the hypothetic plane subsequent thereto (the image plane in the case of the final hypothetic plane). In the case of the hypothetic plane determined with respect to the intersection of the entrance surface and in the case of the stop plane 2, a Z-axis is taken in the direction of the axial principal ray 1 incident thereon. In the case of the hypothetic plane determined with respect to the intersection of the exit surface, a Z-axis is taken in the direction of the axial principal ray 1 exiting from the exit surface. With respect to the first hypothetic plane passing through the intersection between the axial principal ray 1 and the entrance surface (first surface) 11 of the prism 10, a positive direction of the Z-axis is taken in the direction of travel of the axial principal ray 1. With respect to the stop plane 2 and the hypothetic plane regarding the exit surface, a positive direction of the Z-axis is taken in the direction of travel of the axial principal ray 1 in a case where there are an even number of reflections in the optical path from the first hypothetic plane to the stop plane 2 or from the stop plane 2 to the subsequent hypothetic plane. In a case where the number of reflections is an odd number, a positive direction of the Z-axis is taken in an opposite direction to the direction of travel of the axial principal ray 1. A plane containing the Z-axis and the center of the image plane 3 is defined as a YZ-plane. An axis extending through the origin at right angles to the YZ-plane is defined as an X-axis. The direction in which the X-axis extends from the obverse side toward the reverse side of the plane of the figure is defined as a positive direction of the X-axis. An axis that constitutes a right-handed orthogonal coordinate system in combination with the X- and Z-axes is defined as a Y-axis. FIG. 1 shows the hypothetic planes and a coordinate system concerning the first hypothetic plane determined with respect to the intersection of the entrance surface 11. Illustration of the hypothetic planes and the coordinate system is omitted in FIG. 2 and the subsequent figures.

In Example 1 to 15, the decentration of each surface is made in the YZ-plane, and the one and only plane of symmetry of each rotationally asymmetric free-form surface is the YZ-plane.

Regarding decentered surfaces, each surface is given displacements in the X-, Y- and Z-axis directions (X, Y and Z, respectively) of the vertex position of the surface from the origin of the associated coordinate system, and tilt angles (degrees) of the center axis of the surface [the Z-axis of the above equation (a) in regard to free-form surfaces] with respect to the X-, Y- and Z-axes ($\alpha$, $\beta$ and $\gamma$, respectively). In this case, positive $\alpha$ and $\beta$ mean counterclockwise rotation relative to the positive directions of the corresponding axes, and positive $\gamma$ means clockwise rotation relative to the positive direction of the Z-axis.

Among optical-surfaces constituting the optical system in each example, a specific surface (including a hypothetic plane) and a surface subsequent thereto are given a surface separation when these surfaces form a coaxial optical system. In addition, the refractive index and Abbe's number of each medium are given according to the conventional method. It should be noted that the sign of the surface separation is shown to be a positive value in a case where there are an even number of reflections in the optical path from the first hypothetic plane to the reference optical surface (including a hypothetic plane), whereas in a case where the number of reflections is an odd number, the sign of the surface separation is shown to be a negative value. However, the distances in the direction of travel of the axial principal ray 1 are all positive values.

The configuration of each free-form surface used in the present invention is defined by the above equation (a). The Z-axis of the defining equation is the axis of the free-form surface.

In the constituent parameters (shown later), those terms concerning free-form surfaces for which no data is shown are zero. The refractive index is expressed by the refractive index for the spectral d-line (wavelength: 587.56 nanometers). Lengths are given in millimeters.

Free-form surfaces may also be defined by Zernike polynomials. That is, the configuration of a free-form surface may be defined by the following equation (b). The Z-axis of the defining equation (b) is the axis of Zernike polynomial. A rotationally asymmetric surface is defined by polar coordinates of the height of the Z-axis with respect to the XY-plane. In the equation (b), A is the distance from the Z-axis in the XY-plane, and R is the azimuth angle about the Z-axis, which is expressed by the angle of rotation measured from the Z-axis.

$x = R \times \cos(A)$ $y = R \times \sin(A)$ $Z = D_2 +$ $D_3 R \cos(A) + D_4 R \sin(A) +$ $D_5 R^2 \cos(2A) + D_6 (R^2$ $-1) + D_7 R^2 \sin(2A) +$ $D_8 R^3 \cos(3A) + D_9 (3R^3 - 2R)\cos(A) +$ $D_{10}(3R^3 - 2R)\sin(A) + D_{11} R^3 \sin(3A) +$ $D_{12} R^4 \cos(4A) + D_{13}(4R^4 - 3R^2)\cos(2A) +$ $D_{14}(6R^4 - 6R^2 + 1) + D_{15}($ $4R^4 - 3R^2)\sin(2A) +$ $D_{16} R^4 \sin(4A) +$ $D_{17} R^5 \cos(5A) + D_{18}(5R^5 - 4R^3)\cos(3A) +$ $D_{19}(10R^5 - 12R^3 + 3R)\cos(A) +$ $D_{20}(10R^5 - 12R^3 + 3R)\sin(A) +$ $D_{21}(5R^5-4R^3)\sin(3A)+D_{22}R^5\sin(5A)+$ $D_{23}R^6\cos(6A)+D_{24}(6R^6-5R4)\cos(4A)+$ $D_{25}(15R^6-20R^4+6R^2)\cos(2A)+$ $D_{26}(20R^6-30R^4+12R^2-1)+$ $D_{27}(15R^6-20R^4+6R^2)\sin(2A)+$ $D28(6R^6-5R^4)\sin(4A)+D_{29}R^6\sin(6A)$ (b)

In the above equation, to design an optical system symmetric with respect to the X-axis direction, $D_4, D_5, D_6, D_{10}, D_{11}, D_{12}, D_{13}, D_{14}, D_{20}, D_{21}, D_{22}$ ... should be used.

Other examples of surfaces usable in the present invention are expressed by the following defining equation (c):

$Z=\Sigma\Sigma C_{nm}XY$

Assuming that k=7 (polynomial of degree 7), for example, a free-form surface is expressed by an expanded form of the above equation as follows:

$Z=C_2+$ $C_3y+C_4|x|+$ $C_5y^2+C_6y|x|+C_7x^2+$ $C_8y^3+C_9y^2|x|+C_{10}yx^2+C_{11}|x^3|+$ $C_{12}y^4+C_{13}y^3|x|+C_{14}y^2x^2+C_{15}y|x^3|+C_{16}x^4+$ $C_{17}y^5+C_{18}y^4|x|+C_{19}y^3x^2+C_{20}y^2|x^3|+$ $C_{21}yx^4+C_{22}|x^5|+$ $C_{23}y^6+C_{24}y^5|x|+C_{25}y^4x^2+C_{26}y^3|x^3|+$ $C_{27}y^2x^4+C_{28}y|x^5|+C_{29}x^6$ $+C_{30}y^7+C_{31}y^6|x|+C_{32}y^5x^2+C_{33}y^4|x^3|+$ $C_{34}y^3x^4+C_{35}y^2|x^5|+C_{36}yx^6+C_{37}|x^7|$ (c)

Although in the examples of the present invention the surface configuration is expressed by a free-form surface using the above equation (a), it should be noted that the same advantageous effect can be obtained by using the above equation (b) or (c).

In all Examples 1 to 15, photographic field angles are as follows: The horizontal half field angle is 26.3°, and the vertical half field angle is 20.3°. The size of the image pickup device is 3.2×2.4 millimeters. F-number is 2.8. The focal length is equivalent to about 3.27 millimeters. The image-forming optical system according to each example can be applied to other sizes, as a matter of course. The present invention includes not only an image pickup optical system using the image-forming optical system according to the present invention but also an image pickup apparatus incorporating the optical system.

EXAMPLES 1 and 7

FIG. 1 is a sectional view of Example 1 taken along the YZ-plane containing the axial principal ray. The sectional view of Example 7 is similar to FIG. 1. Therefore, illustration of Example 7 is omitted. Constituent parameters of these examples will be shown later. In the constituent parameters, free-form surfaces are denoted by "FFS", and hypothetic planes by "HRP" (Hypothetic Reference Plane). The same shall apply to the other examples.

Examples 1 and 7 each have, in order in which light passes from the object side, an object-side part of a prism 10, a stop 2, an image-side part of the prism 10, and an image plane (image-formation plane) 3. The object-side part of the prism 10 comprises an entrance surface 11 as a first surface, a first reflecting surface 12, and a second reflecting surface 13 formed from the first surface 11, which also serves as the entrance surface 11. The image-side part of the prism 10 comprises a surface C as a third reflecting surface, a surface B as a fourth reflecting surface, and a surface A as an exit surface. Rays from an object enter through the entrance surface 11 and are reflected successively by the first reflecting surface 12 and the second reflecting surface 13. Then, the rays pass through the stop (pupil) 2 and are reflected successively by the surface C and the surface B and then pass through the surface A to form an image on the image plane 3. In the object-side part of the prism 10, the entrance surface 11 and the second reflecting surface 13 are the identical optical surface having both transmitting and reflecting actions. In the image-side part of the prism 10, rays incident on the third reflecting surface C and rays reflected from the fourth reflecting surface B intersect each other.

In the constituent parameters (shown later), the displacements of each of the surface Nos. 2 to 5 are expressed by the amounts of displacement from the hypothetic plane 1 of surface No. 1. The displacements of each of the surface Nos. 6 to 9 are expressed by the amounts of displacement from the stop plane 2 of surface No. 5. The image plane is expressed by only the surface separation along the axial principal ray from the hypothetic plane 2 of surface No. 9.

EXAMPLES 2 and 8

Figure 2:
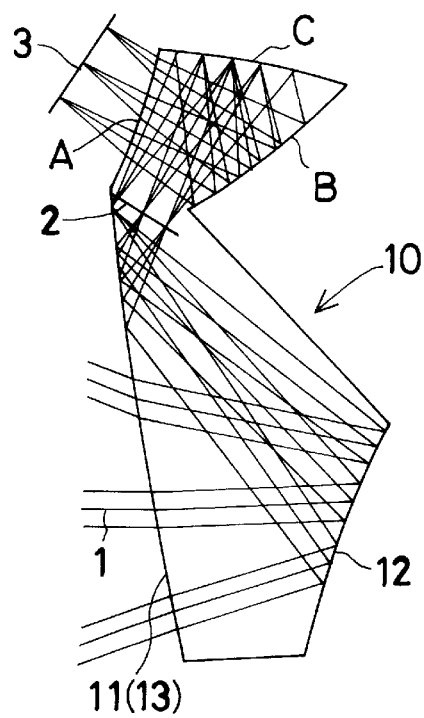
FIG. 2 is a sectional view of an image-forming optical system according to Example 2 of the present invention.

FIG. 2 is a sectional view of Example 2 taken along the YZ-plane containing the axial principal ray. The sectional view of Example 8 is similar to FIG. 2. Therefore, illustration of Example 8 is omitted. Constituent parameters of these examples will be shown later.

Examples 2 and 8 each have, in order in which light passes from the object side, an object-side part of a prism 10, a stop 2, an image-side part of the prism 10, and an image plane (image-formation plane) 3. The object-side part of the prism 10 comprises an entrance surface 11 as a first surface, a first reflecting surface 12, and a second reflecting surface 13 formed from the first surface 11, which also serves as the entrance surface 11. The image-side part of the prism 10 comprises a surface C as a third reflecting surface, a surface B as a fourth reflecting surface, and a surface A as an exit surface. Rays from an object enter through the entrance surface 11 and are reflected successively by the first reflecting surface 12 and the second reflecting surface 13. Then, the rays pass through the stop (pupil) 2 and are reflected successively by the surface C and the surface B and then pass through the surface A to form an image on the image plane 3. In the object-side part of the prism 10, the entrance surface 11 and the second reflecting surface 13 are the identical optical surface having both transmitting and reflecting actions. In the image-side part of the prism 10, rays incident on the third reflecting surface C and rays reflected from the fourth reflecting surface B intersect each other. It should be noted that Examples 2 and 8 differ from Examples 1 and 7 in that the direction in which the rays are reflected from the surface C in Examples 2 and 8 is opposite to that in Examples 1 and 7.

In the constituent parameters (shown later), the displacements of each of the surface Nos. 2 to 5 are expressed by the amounts of displacement from the hypothetic plane 1 of surface No. 1. The displacements of each of the surface Nos.

6 to 9 are expressed by the amounts of displacement from the stop plane 2 of surface No. 5. The image plane is expressed by only the surface separation along the axial principal ray from the hypothetic plane 2 of surface No. 9.

EXAMPLES 3 and 9

Figure 3:
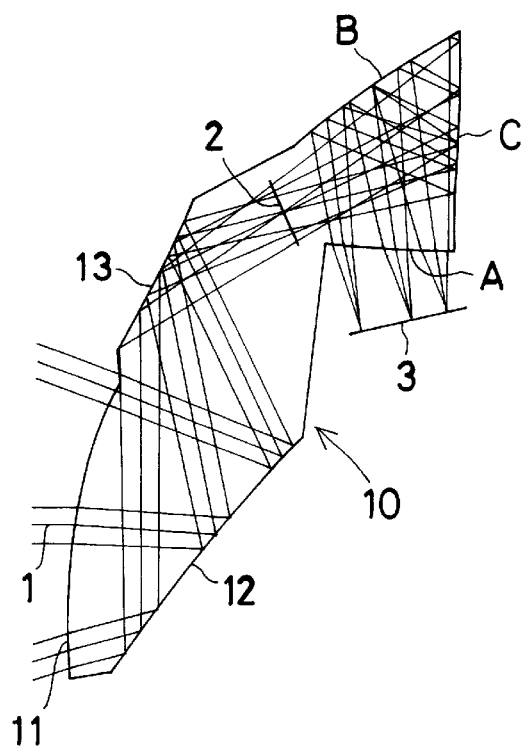
FIG. 3 is a sectional view of an image-forming optical system according to Example 3 of the present invention.

FIG. 3 is a sectional view of Example 3 taken along the YZ-plane containing the axial principal ray. The sectional view of Example 9 is similar to FIG. 3. Therefore, illustration of Example 9 is omitted. Constituent parameters of these examples will be shown later.

Examples 3 and 9 each have, in order in which light passes from the object side, an object-side part of a prism 10, a stop 2, an image-side part of the prism 10, and an image plane (image-formation plane) 3. The object-side part of the prism 10 comprises an entrance surface 11 as a first surface, a first reflecting surface 12, and a second reflecting surface 13. The image-side part of the prism 10 comprises a surface C as a third reflecting surface, a surface B as a fourth reflecting surface, and a surface A as an exit surface. Rays from an object enter through the entrance surface 11 and are reflected successively by the first reflecting surface 12 and the second reflecting surface 13. Then, the rays pass through the stop (pupil) 2 and are reflected successively by the surface C and the surface B and then pass through the surface A to form an image on the image plane 3. In the image-side part of the prism 10, rays incident on the third reflecting surface C and rays reflected from the fourth reflecting surface B intersect each other.

In the constituent parameters (shown later), the displacements of each of the surface Nos. 2 to 5 are expressed by the amounts of displacement from the hypothetic plane 1 of surface No. 1. The displacements of each of the surface Nos. 6 to 9 are expressed by the amounts of displacement from the stop plane 2 of surface No. 5. The image plane is expressed by only the surface separation along the axial principal ray from the hypothetic plane 2 of surface No. 9.

EXAMPLES 4, 10 and 13

Figure 4:
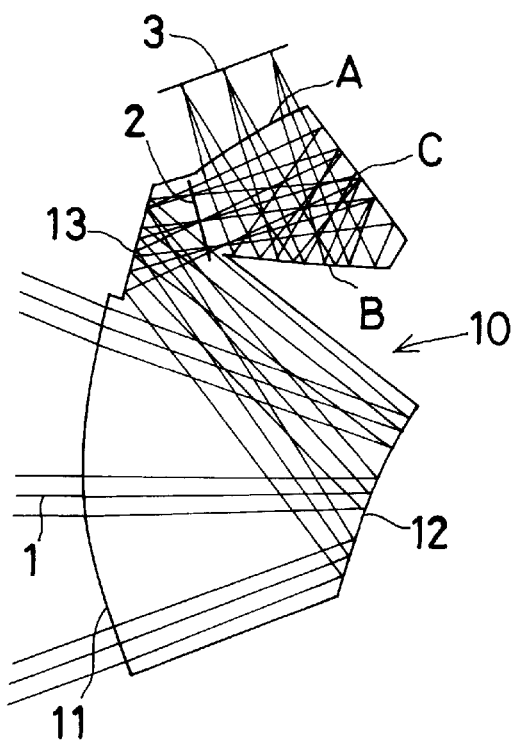
FIG. 4 is a sectional view of an image-forming optical system according to Example 4 of the present invention.
Figure 7:
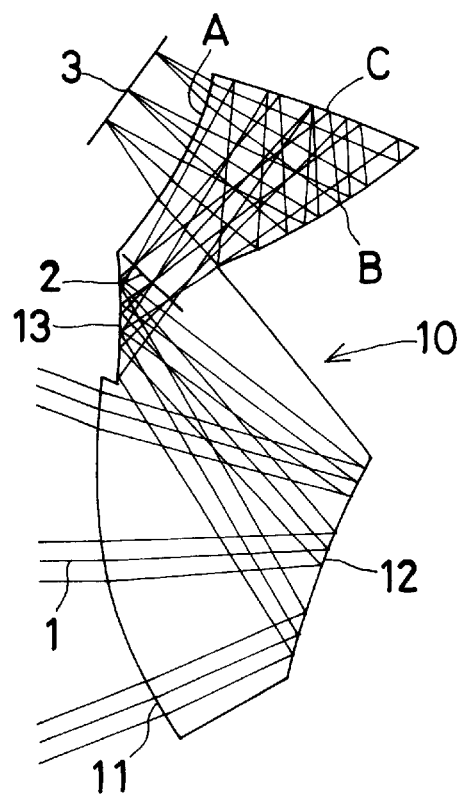
FIG. 7 is a sectional view of an image-forming optical system according to Example 10 of the present invention.

FIGS. 4 and 7 are sectional views of Examples 4 and 10, respectively, taken along the YZ-plane containing the axial principal ray. The sectional view of Example 13 is similar to these figures. Therefore, illustration of Example 13 is omitted. Constituent parameters of these examples will be shown later.

Examples 4, 10 and 13 each have, in order in which light passes from the object side, an object-side part of a prism 10, a stop 2, an image-side part of the prism 10, and an image plane (image-formation plane) 3. The object-side part of the prism 10 comprises an entrance surface 11 as a first surface, a first reflecting surface 12, and a second reflecting surface 13. The image-side part of the prism 10 comprises a surface C as a third reflecting surface, a surface B as a fourth reflecting surface, and a surface A as an exit surface. Rays from an object enter through the entrance surface 11 and are reflected successively by the first reflecting surface 12 and the second reflecting surface 13. Then, the rays pass through the stop (pupil) 2 and are reflected successively by the surface C and the surface B and then pass through the surface A to form an image on the image plane 3. In the image-side part of the prism 10, rays incident on the third reflecting surface C and rays reflected from the fourth reflecting surface B intersect each other. It should be noted that Examples 4, 10 and 13 differ from Examples 3 and 9 in that the direction in which the rays are reflected from the surface C in Examples 4, 10 and 13 is opposite to that in Examples 3 and 9.

In the constituent parameters (shown later), the displacements of each of the surface Nos. 2 to 5 are expressed by the amounts of displacement from the hypothetic plane 1 of surface No. 1. The displacements of each of the surface Nos. 6 to 9 are expressed by the amounts of displacement from the stop plane 2 of surface No. 5. The image plane is expressed by only the surface separation along the axial principal ray from the hypothetic plane 2 of surface No. 9.

EXAMPLES 5, 11 and 14

Figure 5:
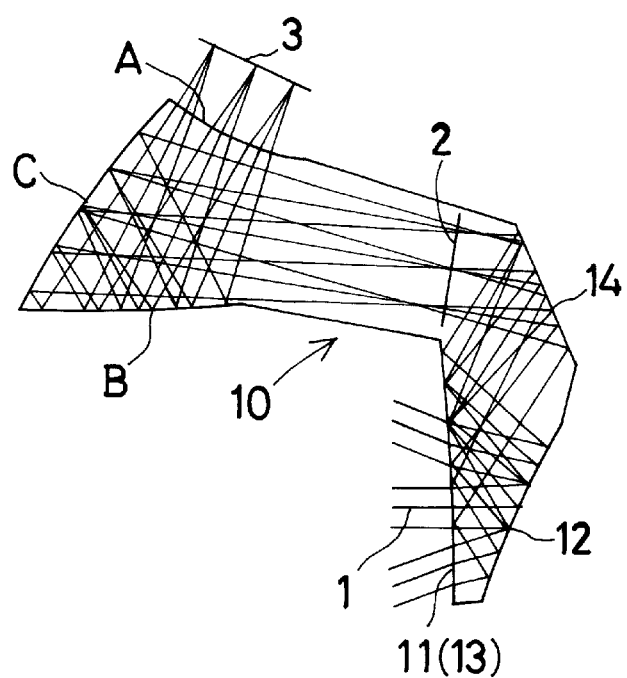
FIG. 5 is a sectional view of an image-forming optical system according to Example 5 of the present invention.

FIG. 5 is a sectional view of Example 5 taken along the YZ-plane containing the axial principal ray. The sectional views of Examples 11 and 14 are similar to FIG. 5. Therefore, illustration of Examples 11 and 14 is omitted. Constituent parameters of these examples will be shown later.

Examples 5, 11 and 14 each have, in order in which light passes from the object side, an object-side part of a prism 10, a stop 2, an image-side part of the prism 10, and an image plane (image-formation plane) 3. The object-side part of the prism 10 comprises an entrance surface 11 as a first surface, a first reflecting surface 12, a second reflecting surface 13 formed from the first surface 11, which also serves as the entrance surface 11, and a third reflecting surface 14. The image-side part of the prism 10 comprises a surface C as a fourth reflecting surface, a surface B as a fifth reflecting surface, and a surface A as an exit surface. Rays from an object enter through the entrance surface 11 and are reflected successively by the first reflecting surface 12, the second reflecting surface 13 and the third reflecting surface 14. Then, the rays pass through the stop (pupil) 2 and are reflected successively by the surface C and the surface B and then pass through the surface A to form an image on the image plane 3. In the object-side part of the prism 10, the entrance surface 11 and the second reflecting surface 13 are the identical optical surface having both transmitting and reflecting actions. In the image-side part of the prism 10, rays incident on the fourth reflecting surface C and rays reflected from the fifth reflecting surface B intersect each other.

In the constituent parameters (shown later), the displacements of each of the surface Nos. 2 to 6 are expressed by the amounts of displacement from the hypothetic plane 1 of surface No. 1. The displacements of each of the surface Nos. 7 to 10 are expressed by the amounts of displacement from the stop plane 2 of surface No. 6. The image plane is expressed by only the surface separation along the axial principal ray from the hypothetic plane 2 of surface No. 10.

EXAMPLES 6, 12 and 15

Figure 6:
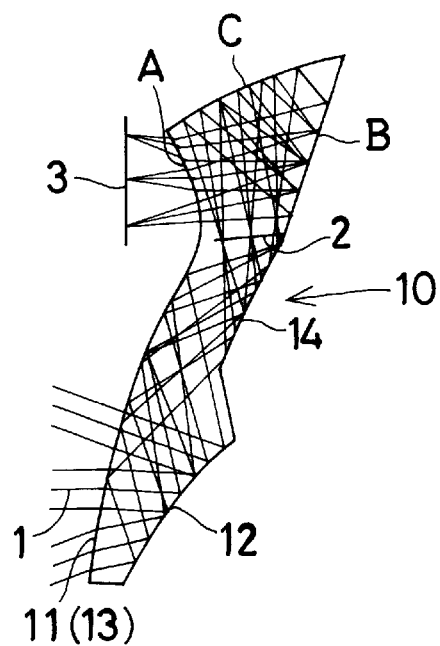
FIG. 6 is a sectional view of an image-forming optical system according to Example 6 of the present invention.
Figure 8:
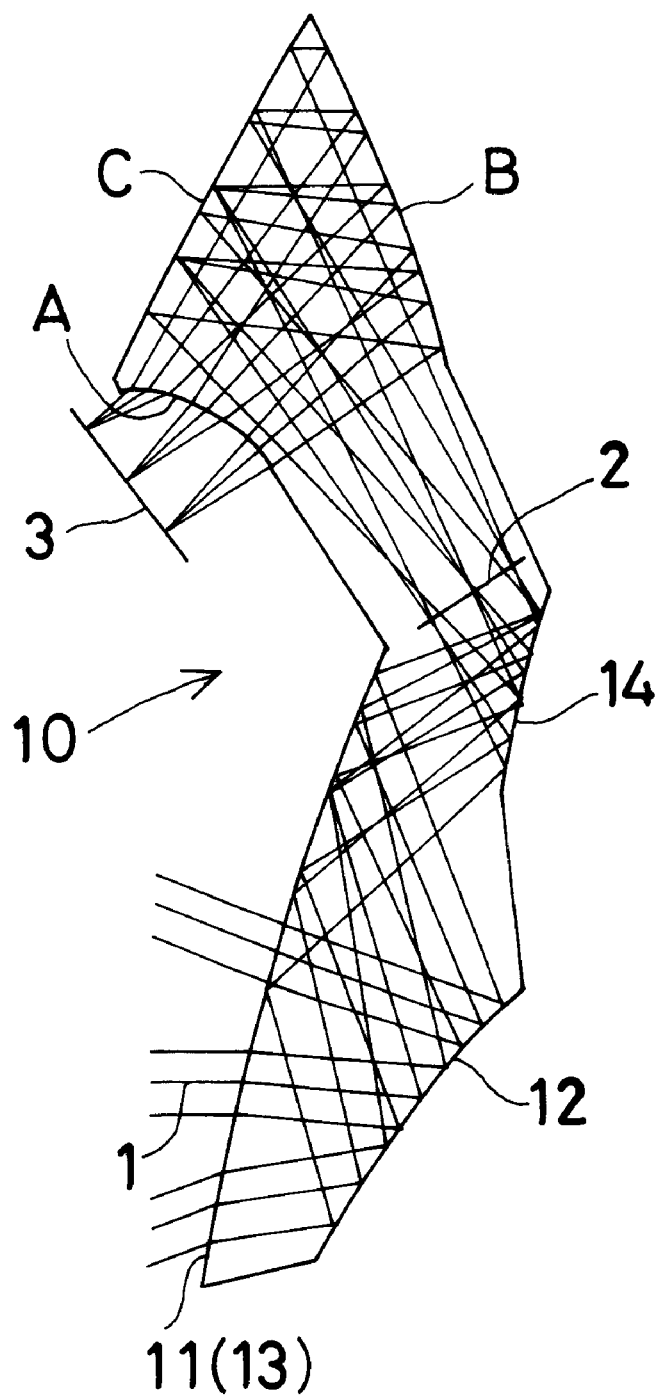
FIG. 8 is a sectional view of an image-forming optical system according to Example 15 of the present invention.

FIGS. 6 and 8 are sectional views of Examples 6 and 15, respectively, taken along the YZ-plane containing the axial principal ray. The sectional view of Example 12 is similar to these figures. Therefore, illustration of Example 12 is omitted. Constituent parameters of these examples will be shown later.

Examples 6, 12 and 15 each have, in order in which light passes from the object side, an object-side part of a prism 10, a stop 2, an image-side part of the prism 10, and an image plane (image-formation plane) 3. The object-side part of the prism 10 comprises an entrance surface 11 as a first surface, a first reflecting surface 12, a second reflecting surface 13 formed from the first surface 11, which also serves as the entrance surface 11, and a third reflecting surface 14. The image-side part of the prism 10 comprises a surface C as a fourth reflecting surface, a surface B as a fifth reflecting surface, and a surface A as an exit surface. Rays from an object enter through the entrance surface 11 and are reflected successively by the first reflecting surface 12, the second reflecting surface 13 and the third reflecting surface 14. Then, the rays pass through the stop (pupil) 2 and are reflected successively by the surface C and the surface B and then pass through the surface A to form an image on the image plane 3. In the object-side part of the prism 10, the entrance surface 11 and the second reflecting surface 13 are the identical optical surface having both transmitting and reflecting actions. In the image-side part of the prism 10, rays incident on the fourth reflecting surface C and rays reflected from the fifth reflecting surface B intersect each other. It should be noted that Examples 6, 12 and 15 differ from Examples 5, 11 and 14 in that the direction in which the rays are reflected from the surface C in Examples 6, 12 and 15 is opposite to that in Examples 5, 11 and 14.

In the constituent parameters (shown later), the displacements of each of the surface Nos. 2 to 6 are expressed by the amounts of displacement from the hypothetic plane 1 of surface No. 1. The displacements of each of the surface Nos. 7 to 10 are expressed by the amounts of displacement from the stop plane 2 of surface No. 6. The image plane is expressed by only the surface separation along the axial principal ray from the hypothetic plane 2 of surface No. 10.

Constituent parameters in the foregoing Examples 1 to 15 are shown below. In the tables below, "FFS" denotes a free-form surface, and "HRP" denotes a hypothetic plane.

EXAMPLE 1

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | ∞ (Stop) | | (3) | 1.4924 | 57.6 |
| 6 | FFS③ | | (4) | 1.4924 | 57.6 |
| 7 | FFS④ | | (5) | 1.4924 | 57.6 |
| 8 | 73.54 | | (6) | | |
| 9 | ∞ (HRP2) | 2.41 | (7) | | |
| Image plane | ∞ | | | | |

FFS①
$C_4$  $2.6439 \times 10^{-2}$  $C_6$  $7.9226 \times 10^{-3}$
FFS②
$C_4$  $4.0609 \times 10^{-2}$  $C_6$  $3.3603 \times 10^{-2}$
FFS③
$C_4$  $-5.9833 \times 10^{-3}$  $C_6$  $-2.1530 \times 10^{-2}$
FFS④
$C_4$  $2.7734 \times 10^{-2}$  $C_6$  $9.1914 \times 10^{-4}$
Displacement and tilt(1)
X  0.00  Y  4.02  Z  1.04
α  −16.44  β  0.00  γ  0.00
Displacement and tilt(2)
X  0.00  Y  −0.18  Z  2.45
α  −37.84  β  0.00  γ  0.00
Displacement and tilt(3)
X  0.00  Y  8.69  Z  6.90
α  38.59  β  0.00  γ  0.00
Displacement and tilt(4)
X  0.00  Y  0.00  Z  6.82
α  −18.97  β  0.00  γ  0.00
Displacement and tilt(5)
X  0.00  Y  3.09  Z  2.85
α  −65.23  β  0.00  γ  0.00

-continued

Displacement and tilt(6)
X  0.00  Y  −2.56  Z  2.60
α  −106.23  β  0.00  γ  0.00
Displacement and tilt(7)
X  0.00  Y  −2.56  Z  2.60
α  −85.52  β  0.00  γ  0.00

EXAMPLE 2

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | ∞ (Stop) | | (3) | 1.4924 | 57.6 |
| 6 | FFS③ | | (4) | 1.4924 | 57.6 |
| 7 | FFS④ | | (5) | 1.4924 | 57.6 |
| 8 | 31.83 | | (6) | | |
| 9 | ∞ (HRP2) | 2.41 | (7) | | |
| Image plane | ∞ | | | | |

FFS①
$C_4$  $1.0505 \times 10^{-2}$  $C_6$  $3.8788 \times 10^{-3}$
FFS②
$C_4$  $1.8664 \times 10^{-2}$  $C_6$  $1.2463 \times 10^{-2}$
FFS③
$C_4$  $-1.7214 \times 10^{-2}$  $C_6$  $-1.1967 \times 10^{-2}$
FFS④
$C_4$  $1.8563 \times 10^{-2}$  $C_6$  $1.7741 \times 10^{-2}$
Displacement and tilt(1)
X  0.00  Y  8.07  Z  −1.41
α  8.10  β  0.00  γ  0.00
Displacement and tilt(2)
X  0.00  Y  0.44  Z  6.39
α  −20.24  β  0.00  γ  0.00
Displacement and tilt(3)
X  0.00  Y  9.38  Z  −0.67
α  60.58  β  0.00  γ  0.00
Displacement and tilt(4)
X  0.00  Y  0.00  Z  5.62
α  20.78  β  0.00  γ  0.00
Displacement and tilt(5)
X  0.00  Y  −2.29  Z  3.04
α  66.52  β  0.00  γ  0.00
Displacement and tilt(6)
X  0.00  Y  1.70  Z  2.94
α  103.30  β  0.00  γ  0.00
Displacement and tilt(7)
X  0.00  Y  1.70  Z  2.94
α  85.51  β  0.00  γ  0.00

EXAMPLE 3

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS③ | | (3) | 1.4924 | 57.6 |
| 5 | ∞ (Stop) | | (4) | 1.4924 | 57.6 |
| 6 | FFS④ | | (5) | 1.4924 | 57.6 |

-continued

| | | | | | |
|---|---|---|---|---|---|
| 7 | FFS⑤ | | (6) | 1.4924 | 57.6 |
| 8 | −34.67 | | (7) | | |
| 9 | ∞ (HRP2) | 2.32 | (8) | | |
| Image plane | ∞ | | | | |

FFS①
$C_4$  $5.1017 \times 10^{-2}$  $C_6$  $2.7482 \times 10^{-2}$
FFS②
$C_4$  $4.4288 \times 10^{-2}$  $C_6$  $5.8438 \times 10^{-3}$
FFS③
$C_4$  $1.9287 \times 10^{-2}$  $C_6$  $-9.0886 \times 10^{-3}$
FFS④
$C_4$  $-1.0634 \times 10^{-2}$  $C_6$  $-1.8892 \times 10^{-2}$
FFS⑤
$C_4$  $2.1589 \times 10^{-2}$  $C_6$  $1.2903 \times 10^{-2}$
Displacement and tilt(1)
  X    0.00   Y    0.00   Z    0.00
  α  −10.17   β    0.00   γ    0.00
Displacement and tilt(2)
  X    0.00   Y   −0.27   Z    4.63
  α  −40.38   β    0.00   γ    0.00
Displacement and tilt(3)
  X    0.00   Y    8.09   Z    2.76
  α  −26.12   β    0.00   γ    0.00
Displacement and tilt(4)
  X    0.00   Y    9.92   Z    6.66
  α   25.15   β    0.00   γ    0.00
Displacement and tilt(5)
  X    0.00   Y    0.00   Z    6.18
  α  −26.28   β    0.00   γ    0.00
Displacement and tilt(6)
  X    0.00   Y    2.38   Z    4.36
  α  −80.23   β    0.00   γ    0.00
Displacement and tilt(7)
  X    0.00   Y   −2.63   Z    2.74
  α −118.42   β    0.00   γ    0.00
Displacement and tilt(8)
  X    0.00   Y   −2.54   Z    2.36
  α −102.61   β    0.00   γ    0.00

EXAMPLE 4

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS③ | | (3) | 1.4924 | 57.6 |
| 5 | ∞ (Stop) | | (4) | | |
| 6 | FFS④ | | (5) | 1.4924 | 57.6 |
| 7 | FFS⑤ | | (6) | 1.4924 | 57.6 |
| 8 | −28.23 | | (7) | | |
| 9 | ∞ (HRP2) | 2.21 | (8) | | |
| Image plane | ∞ | | | | |

FFS①
$C_4$  $3.6103 \times 10^{-2}$  $C_6$  $3.7578 \times 10^{-2}$
FFS②
$C_4$  $3.2368 \times 10^{-2}$  $C_6$  $2.5846 \times 10^{-2}$
FFS③
$C_4$  $1.4152 \times 10^{-2}$  $C_6$  $1.0130 \times 10^{-2}$
FFS④
$C_4$  $-1.5351 \times 10^{-2}$  $C_6$  $-1.2774 \times 10^{-2}$
FFS⑤
$C_4$  $1.8146 \times 10^{-2}$  $C_6$  $1.4305 \times 10^{-2}$
Displacement and tilt(1)
  X    0.00   Y    0.00   Z    0.00
  α    5.97   β    0.00   γ    0.00
Displacement and tilt(2)
  X    0.00   Y    0.29   Z    8.38
  α  −21.81   β    0.00   γ    0.00
Displacement and tilt(3)
  X    0.00   Y    7.45   Z    1.36
  α  −13.97   β    0.00   γ    0.00
Displacement and tilt(4)
  X    0.00   Y    8.01   Z    3.13
  α   17.65   β    0.00   γ    0.00
Displacement and tilt(5)
  X    0.00   Y    0.00   Z    4.83
  α   20.94   β    0.00   γ    0.00
Displacement and tilt(6)
  X    0.00   Y   −2.03   Z    2.56
  α   69.43   β    0.00   γ    0.00
Displacement and tilt(7)
  X    0.00   Y    1.85   Z    2.09
  α  103.84   β    0.00   γ    0.00
Displacement and tilt(8)
  X    0.00   Y    1.86   Z    2.30
  α   93.58   β    0.00   γ    0.00

EXAMPLE 5

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | FFS③ | | (3) | 1.4924 | 57.6 |
| 6 | ∞ (Stop) | | (4) | 1.4924 | 57.6 |
| 7 | FFS④ | | (5) | 1.4924 | 57.6 |
| 8 | FFS⑤ | | (6) | 1.4924 | 57.6 |
| 9 | FFS⑥ | | (7) | | |
| 10 | ∞ (HRP2) | −2.16 | (8) | | |
| Image plane | ∞ | | | | |

FFS①
$C_4$  $4.7826 \times 10^{-3}$  $C_6$  $-1.0454 \times 10^{-2}$
FFS②
$C_4$  $3.6891 \times 10^{-2}$  $C_6$  $1.2733 \times 10^{-2}$
FFS③
$C_4$  $-1.6084 \times 10^{-2}$  $C_6$  $-1.3974 \times 10^{-2}$
FFS④
$C_4$  $1.7544 \times 10^{-2}$  $C_6$  $1.6602 \times 10^{-2}$
FFS⑤
$C_4$  $-1.2423 \times 10^{-2}$  $C_6$  $-7.7482 \times 10^{-3}$
FFS⑥
$C_4$  $-3.9833 \times 10^{-2}$  $C_6$  $-6.0704 \times 10^{-2}$
Displacement and tilt(1)
  X    0.00   Y    2.25   Z   −0.13
  α    4.72   β    0.00   γ    0.00
Displacement and tilt(2)
  X    0.00   Y    0.02   Z    1.82
  α  −24.02   β    0.00   γ    0.00
Displacement and tilt(3)
  X    0.00   Y    6.36   Z    2.42
  α   24.37   β    0.00   γ    0.00
Displacement and tilt(4)
  X    0.00   Y    6.79   Z   −0.17
  α   −9.40   β    0.00   γ    0.00
Displacement and tilt(5)
  X    0.00   Y    0.00   Z  −10.80
  α  −25.46   β    0.00   γ    0.00
Displacement and tilt(6)
  X    0.00   Y   −2.64   Z   −8.65
  α  −78.40   β    0.00   γ    0.00
Displacement and tilt(7)
  X    0.00   Y    2.73   Z   −7.13
  α −107.91   β    0.00   γ    0.00

-continued

Displacement and tilt(8)
X    0.00   Y   2.73   Z   −7.13
α  −104.86  β   0.00   γ    0.00

EXAMPLE 6

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | FFS③ | | (3) | 1.4924 | 57.6 |
| 6 | ∞ (Stop) | | (4) | 1.4924 | 57.6 |
| 7 | FFS④ | | (5) | 1.4924 | 57.6 |
| 8 | FFS⑤ | | (6) | 1.4924 | 57.6 |
| 9 | FFS⑥ | | (7) | | |
| 10 | ∞ (HRP2) | −2.00 | (8) | | |
| Image plane | ∞ | | | | |

FFS①
$C_4$  $2.1296 \times 10^{-2}$  $C_6$  $2.4788 \times 10^{-2}$
FFS②
$C_4$  $2.3940 \times 10^{-2}$  $C_6$  $4.0754 \times 10^{-2}$
FFS③
$C_4$  $8.1786 \times 10^{-3}$  $C_6$  $2.1979 \times 10^{-2}$
FFS④
$C_4$  $1.7186 \times 10^{-2}$  $C_6$  $3.8279 \times 10^{-2}$
FFS⑤
$C_4$  $-2.6631 \times 10^{-2}$  $C_6$  $-2.5734 \times 10^{-3}$
FFS⑥
$C_4$  $3.4447 \times 10^{-3}$  $C_6$  $-1.1766 \times 10^{-2}$
Displacement and tilt(1)
X    0.00   Y   4.00   Z   1.25
α  −23.32   β   0.00   γ   0.00
Displacement and tilt(2)
X    0.00   Y  −0.15   Z   2.27
α  −40.04   β   0.00   γ   0.00
Displacement and tilt(3)
X    0.00   Y   5.83   Z   4.47
α  −27.60   β   0.00   γ   0.00
Displacement and tilt(4)
X    0.00   Y   7.34   Z   4.33
α  −84.78   β   0.00   γ   0.00
Displacement and tilt(5)
X    0.00   Y   0.00   Z  −4.24
α   19.91   β   0.00   γ   0.00
Displacement and tilt(6)
X    0.00   Y   1.90   Z  −1.97
α   66.04   β   0.00   γ   0.00
Displacement and tilt(7)
X    0.00   Y  −1.55   Z  −1.83
α  106.80   β   0.00   γ   0.00
Displacement and tilt(8)
X    0.00   Y  −1.55   Z  −1.83
α   84.78   β   0.00   γ   0.00

EXAMPLE 7

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | ∞ (Stop) | | (3) | 1.4924 | 57.6 |
| 6 | FFS③ | | (4) | 1.4924 | 57.6 |
| 7 | FFS④ | | (5) | 1.4924 | 57.6 |
| 8 | | 8.92 | (6) | | |
| 9 | ∞ (HRP2) | 2.22 | (7) | | |
| Image plane | ∞ | | | | |

FFS①
$C_4$  $2.5961 \times 10^{-2}$  $C_6$  $1.5014 \times 10^{-2}$  $C_8$  $5.6194 \times 10^{-5}$
$C_{10}$  $-1.1753 \times 10^{-3}$
FFS②
$C_4$  $4.3736 \times 10^{-2}$  $C_6$  $4.1967 \times 10^{-2}$  $C_8$  $9.5457 \times 10^{-4}$
$C_{10}$  $-3.8192 \times 10^{-3}$
FFS③
$C_4$  $-1.4677 \times 10^{-2}$  $C_6$  $-7.1640 \times 10^{-3}$  $C_8$  $1.1987 \times 10^{-3}$
$C_{10}$  $-1.4720 \times 10^{-4}$
FFS④
$C_4$  $2.2962 \times 10^{-2}$  $C_6$  $2.1266 \times 10^{-2}$  $C_8$  $4.1512 \times 10^{-4}$
$C_{10}$  $-7.5793 \times 10^{-4}$
Displacement and tilt(1)
X    0.00   Y   2.79   Z   0.48
α  −12.75   β   0.00   γ   0.00
Displacement and tilt(2)
X    0.00   Y  −0.07   Z   1.90
α  −32.82   β   0.00   γ   0.00
Displacement and tilt(3)
X    0.00   Y   8.13   Z   7.29
α   38.07   β   0.00   γ   0.00
Displacement and tilt(4)
X    0.00   Y   0.00   Z   9.34
α  −25.11   β   0.00   γ   0.00
Displacement and tilt(5)
X    0.00   Y   2.63   Z   7.16
α  −81.51   β   0.00   γ   0.00
Displacement and tilt(6)
X    0.00   Y  −2.44   Z   5.03
α −117.16   β   0.00   γ   0.00
Displacement and tilt(7)
X    0.00   Y  −2.44   Z   5.03
α −110.65   β   0.00   γ   0.00

EXAMPLE 8

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | ∞ (Stop) | | (3) | 1.4924 | 57.6 |
| 6 | FFS③ | | (4) | 1.4924 | 57.6 |
| 7 | FFS④ | | (5) | 1.4924 | 57.6 |
| 8 | FFS⑤ | | (6) | | |
| 9 | ∞ (HRP2) | 2.26 | (7) | | |
| Image plane | ∞ | | | | |

FFS①
$C_4$  $2.3679 \times 10^{-2}$  $C_6$  $9.5574 \times 10^{-3}$  $C_8$  $2.1880 \times 10^{-4}$
$C_{10}$  $-5.1754 \times 10^{-4}$
FFS②
$C_4$  $3.5018 \times 10^{-2}$  $C_6$  $2.9912 \times 10^{-2}$  $C_8$  $1.3808 \times 10^{-3}$
$C_{10}$  $-1.3308 \times 10^{-3}$
FFS③
$C_4$  $-2.2815 \times 10^{-2}$  $C_6$  $-1.7935 \times 10^{-2}$  $C_8$  $-3.8274 \times 10^{-4}$
$C_{10}$  $-3.4017 \times 10^{-5}$
FFS④

-continued

| | | | | | | |
|---|---|---|---|---|---|---|
| $C_4$ | $1.1424 \times 10^{-2}$ | $C_6$ | $9.7322 \times 10^{-2}$ | $C_8$ | $-9.1508 \times 10^{-2}$ | |
| $C_{10}$ | $2.5355 \times 10^{-4}$ | | | | | |
| FFS⑤ | | | | | | |
| $C_4$ | $-1.0675 \times 10^{-2}$ | $C_6$ | $2.3608 \times 10^{-2}$ | $C_8$ | $-3.1240 \times 10^{-2}$ | |

Displacement and tilt(1)
X   0.00   Y   3.09   Z   0.47
α  −10.74  β   0.00   γ   0.00
Displacement and tilt(2)
X   0.00   Y  −0.07   Z   1.85
α  −34.31  β   0.00   γ   0.00
Displacement and tilt(3)
X   0.00   Y  12.58   Z   9.97
α   45.00  β   0.00   γ   0.00
Displacement and tilt(4)
X   0.00   Y   0.00   Z   5.68
α   27.20  β   0.00   γ   0.00
Displacement and tilt(5)
X   0.00   Y  −2.25   Z   4.07
α   82.51  β   0.00   γ   0.00
Displacement and tilt(6)
X   0.00   Y  −2.25   Z   2.37
α  102.32  β   0.00   γ   0.00
Displacement and tilt(7)
X   0.00   Y   2.25   Z   2.37
α  114.77  β   0.00   γ   0.00

EXAMPLE 9

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS③ | | (3) | 1.4924 | 57.6 |
| 5 | ∞ (Stop) | | (4) | 1.4924 | 57.6 |
| 6 | FFS④ | | (5) | 1.4924 | 57.6 |
| 7 | FFS⑤ | | (6) | 1.4924 | 57.6 |
| 8 | 11.35 | | (7) | | |
| 9 | ∞ (HRP2) | 2.05 | (8) | | |
| Image plane | ∞ | | | | |

FFS①
$C_4$  $2.0299 \times 10^{-2}$  $C_6$  $2.1011 \times 10^{-2}$  $C_8$  $3.7792 \times 10^{-3}$
$C_{10}$  $1.1967 \times 10^{-3}$
FFS②
$C_4$  $2.7527 \times 10^{-2}$  $C_6$  $9.6524 \times 10^{-3}$  $C_8$  $1.8426 \times 10^{-3}$
$C_{10}$  $4.8011 \times 10^{-4}$
FFS③
$C_4$  $1.9362 \times 10^{-2}$  $C_6$  $-2.0125 \times 10^{-3}$  $C_8$  $9.2062 \times 10^{-4}$
$C_{10}$  $1.7905 \times 10^{-4}$
FFS④
$C_4$  $-1.0067 \times 10^{-2}$  $C_6$  $-1.7791 \times 10^{-3}$  $C_8$  $1.2309 \times 10^{-3}$
$C_{10}$  $3.6169 \times 10^{-4}$
FFS⑤
$C_4$  $2.7337 \times 10^{-2}$  $C_6$  $1.6341 \times 10^{-2}$  $C_8$  $3.7921 \times 10^{-4}$
$C_{10}$  $-1.2527 \times 10^{-4}$ Displacement and tilt(1)
X   0.00   Y   0.00   Z   0.00
α   0.71   β   0.00   γ   0.00
Displacement and tilt(2)
X   0.00   Y   0.01   Z   3.45
α  −39.92  β   0.00   γ   0.00
Displacement and tilt(3)
X   0.00   Y  10.27   Z   1.66
α  −19.10  β   0.00   γ   0.00
Displacement and tilt(4)
X   0.00   Y  13.38   Z   5.12
α   41.87  β   0.00   γ   0.00
Displacement and tilt(5)
X   0.00   Y   0.00   Z   6.16
α  −26.84  β   0.00   γ   0.00
Displacement and tilt(6)
X   0.00   Y   2.23   Z   4.52
α  −81.76  β   0.00   γ   0.00
Displacement and tilt(7)
X   0.00   Y  −2.17   Z   2.93
α −110.12  β   0.00   γ   0.00
Displacement and tilt(8)
X   0.00   Y  −2.14   Z   2.85
α −109.73  β   0.00   γ   0.00

EXAMPLE 10

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS③ | | (3) | 1.4924 | 57.6 |
| 5 | ∞ (Stop) | | (4) | 1.4924 | 57.6 |
| 6 | FFS④ | | (5) | 1.4924 | 57.6 |
| 7 | FFS⑤ | | (6) | 1.4924 | 57.6 |
| 8 | 11.50 | | (7) | | |
| 9 | ∞ (HRP2) | 2.41 | (8) | | |
| Image plane | ∞ | | | | |

FFS①
$C_4$  $8.9203 \times 10^{-3}$  $C_6$  $3.9004 \times 10^{-2}$  $C_8$  $2.9860 \times 10^{-3}$
$C_{10}$  $-1.3651 \times 10^{-3}$
FFS②
$C_4$  $2.6402 \times 10^{-2}$  $C_6$  $1.5704 \times 10^{-2}$  $C_8$  $1.2944 \times 10^{-3}$
$C_{10}$  $-1.2656 \times 10^{-4}$
FFS③
$C_4$  $1.3314 \times 10^{-2}$  $C_6$  $-5.0059 \times 10^{-3}$  $C_8$  $-2.3594 \times 10^{-4}$
$C_{10}$  $6.0685 \times 10^{-4}$
FFS④
$C_4$  $-1.7132 \times 10^{-2}$  $C_6$  $-1.2802 \times 10^{-2}$  $C_8$  $-8.1788 \times 10^{-4}$
$C_{10}$  $1.1746 \times 10^{-3}$
FFS⑤
$C_4$  $1.8996 \times 10^{-2}$  $C_6$  $2.4503 \times 10^{-2}$  $C_8$  $-6.0699 \times 10^{-4}$
$C_{10}$  $1.7658 \times 10^{-3}$ Displacement and tilt(1)
X   0.00   Y   0.00   Z   0.00
α   9.49   β   0.00   γ   0.00
Displacement and tilt(2)
X   0.00   Y   0.36   Z   6.63
α  −22.14  β   0.00   γ   0.00
Displacement and tilt(3)
X   0.00   Y   7.07   Z   0.46
α   −0.08  β   0.00   γ   0.00
Displacement and tilt(4)
X   0.00   Y   8.08   Z   1.39
α   47.26  β   0.00   γ   0.00
Displacement and tilt(5)
X   0.00   Y   0.00   Z   6.99
α   23.53  β   0.00   γ   0.00
Displacement and tilt(6)
X   0.00   Y  −2.43   Z   4.73
α   73.73  β   0.00   γ   0.00
Displacement and tilt(7)
X   0.00   Y   1.96   Z   3.93
α  109.47  β   0.00   γ   0.00
Displacement and tilt(8)
X   0.00   Y   1.97   Z   4.04
α   95.84  β   0.00   γ   0.00

EXAMPLE 11

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | FFS③ | | (3) | 1.4924 | 57.6 |
| 6 | ∞ (Stop) | | (4) | | |
| 7 | FFS④ | | (5) | 1.4924 | 57.6 |
| 8 | FFS⑤ | | (6) | 1.4924 | 57.6 |
| 9 | FFS⑥ | | (7) | | |
| 10 | ∞ (HRP2) | −2.14 | (8) | | |
| Image plane | ∞ | | | | |

FFS①
$C_4$  $3.4578 \times 10^{-2}$  $C_6$  $1.4392 \times 10^{-2}$  $C_8$  $-1.5830 \times 10^{-3}$
$C_{10}$  $-6.4400 \times 10^{-4}$
FFS②
$C_4$  $3.6730 \times 10^{-2}$  $C_6$  $3.9223 \times 10^{-2}$  $C_8$  $-2.8253 \times 10^{-3}$
$C_{10}$  $-1.9571 \times 10^{-3}$
FFS③
$C_4$  $2.0240 \times 10^{-2}$  $C_6$  $1.1058 \times 10^{-3}$  $C_8$  $1.5508 \times 10^{-4}$
$C_{10}$  $2.4574 \times 10^{-4}$
FFS④
$C_4$  $1.7872 \times 10^{-2}$  $C_6$  $1.2937 \times 10^{-2}$  $C_8$  $9.4982 \times 10^{-4}$
$C_{10}$  $3.9786 \times 10^{-4}$
FFS⑤
$C_4$  $-2.2246 \times 10^{-2}$  $C_6$  $-1.9019 \times 10^{-2}$  $C_8$  $3.4959 \times 10^{-4}$
$C_{10}$  $-2.0661 \times 10^{-4}$
FFS⑥
$C_4$  $-3.4740 \times 10^{-2}$  $C_6$  $-1.2443 \times 10^{-1}$  $C_8$  $1.3265 \times 10^{-4}$
$C_{10}$  $-9.8514 \times 10^{-3}$
Displacement and tilt(1)
X  0.00  Y  2.21  Z  0.09
α  −4.39  β  0.00  γ  0.00
Displacement and tilt(2)
X  0.00  Y  0.00  Z  1.65
α  −27.40  β  0.00  γ  0.00
Displacement and tilt(3)
X  0.00  Y  5.69  Z  3.46
α  −3.64  β  0.00  γ  0.00
Displacement and tilt(4)
X  0.00  Y  10.50  Z  −0.13
α  −53.22  β  0.00  γ  0.00
Displacement and tilt(5)
X  0.00  Y  0.00  Z  −8.34
α  −26.53  β  0.00  γ  0.00
Displacement and tilt(6)
X  0.00  Y  −2.61  Z  −6.38
α  −79.50  β  0.00  γ  0.00
Displacement and tilt(7)
X  0.00  Y  2.45  Z  −4.93
α  −106.11  β  0.00  γ  0.00
Displacement and tilt(8)
X  0.00  Y  2.45  Z  −4.93
α  −105.85  β  0.00  γ  0.00

EXAMPLE 12

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | FFS③ | | (3) | 1.4924 | 57.6 |
| 6 | ∞ (Stop) | | (4) | 1.4924 | 57.6 |
| 7 | FFS④ | | (5) | 1.4924 | 57.6 |
| 8 | FFS⑤ | | (6) | 1.4924 | 57.6 |
| 9 | FFS⑥ | | (7) | | |
| 10 | ∞ (HRP2) | −2.00 | (8) | | |
| Image plane | ∞ | | | | |

FFS①
$C_4$  $3.7649 \times 10^{-2}$  $C_6$  $1.7817 \times 10^{-2}$  $C_8$  $4.8828 \times 10^{-4}$
$C_{10}$  $-2.8895 \times 10^{-5}$
FFS②
$C_4$  $3.9048 \times 10^{-2}$  $C_6$  $3.3816 \times 10^{-2}$  $C_8$  $5.4451 \times 10^{-4}$
$C_{10}$  $-1.2081 \times 10^{-3}$
FFS③
$C_4$  $2.6818 \times 10^{-2}$  $C_6$  $1.1863 \times 10^{-2}$  $C_8$  $4.8350 \times 10^{-5}$
$C_{10}$  $6.3702 \times 10^{-4}$
FFS④
$C_4$  $1.5997 \times 10^{-2}$  $C_6$  $2.9264 \times 10^{-3}$  $C_8$  $-2.2617 \times 10^{-3}$
$C_{10}$  $-1.3131 \times 10^{-3}$
FFS⑤
$C_4$  $-3.0842 \times 10^{-2}$  $C_6$  $-3.2950 \times 10^{-2}$  $C_8$  $-1.0973 \times 10^{-3}$
$C_{10}$  $-5.2443 \times 10^{-4}$
FFS⑥
$C_4$  $-9.8256 \times 10^{-2}$  $C_6$  $-1.6629 \times 10^{-1}$  $C_8$  $-7.3379 \times 10^{-3}$
$C_{10}$  $-2.0373 \times 10^{-2}$
Displacement and tilt(1)
X  0.00  Y  6.79  Z  1.55
α  −19.94  β  0.00  γ  0.00
Displacement and tilt(2)
X  0.00  Y  −0.14  Z  4.06
α  −36.01  β  0.00  γ  0.00
Displacement and tilt(3)
X  0.00  Y  9.26  Z  5.79
α  −9.94  β  0.00  γ  0.00
Displacement and tilt(4)
X  0.00  Y  10.97  Z  4.36
α  −50.10  β  0.00  γ  0.00
Displacement and tilt(5)
X  0.00  Y  0.00  Z  −6.17
α  28.58  β  0.00  γ  0.00
Displacement and tilt(6)
X  0.00  Y  2.46  Z  −4.58
α  82.38  β  0.00  γ  0.00
Displacement and tilt(7)
X  0.00  Y  −1.83  Z  −3.22
α  114.82  β  0.00  γ  0.00
Displacement and tilt(8)
X  0.00  Y  −1.83  Z  −3.22
α  104.01  β  0.00  γ  0.00

EXAMPLE 13

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS③ | | (3) | 1.4924 | 57.6 |
| 5 | ∞ (Stop) | | (4) | 1.4924 | 57.6 |
| 6 | FFS④ | | (5) | 1.4924 | 57.6 |
| 7 | FFS⑤ | | (6) | 1.4924 | 57.6 |
| 8 | FFS⑥ | | (7) | | |
| 9 | ∞ (HRP2) | 3.05 | (8) | | |
| Image plane | ∞ | | | | |

FFS①
$C_4$  $1.8239 \times 10^{-2}$  $C_6$  $1.4286 \times 10^{-2}$  $C_8$  $1.0132 \times 10^{-3}$
$C_{10}$  $-2.3081 \times 10^{-4}$  $C_{13}$  $-1.7601 \times 10^{-4}$ -continued FFS①
| | | | | | |
|---|---|---|---|---|---|
| $C_4$ | $3.7683 \times 10^{-2}$ | $C_6$ | $1.0427 \times 10^{-2}$ | $C_8$ | $2.3263 \times 10^{-4}$ |
| $C_{10}$ | $3.4809 \times 10^{-4}$ | $C_{11}$ | $-3.5873 \times 10^{-4}$ | $C_{13}$ | $-2.2847 \times 10^{-4}$ |
| $C_{15}$ | $-7.4601 \times 10^{-5}$ | | | | |

FFS③
| | | | | | |
|---|---|---|---|---|---|
| $C_4$ | $2.2486 \times 10^{-2}$ | $C_6$ | $-5.9061 \times 10^{-3}$ | $C_8$ | $-9.8429 \times 10^{-4}$ |
| $C_{10}$ | $-1.4520 \times 10^{-4}$ | $C_{11}$ | $-3.9632 \times 10^{-4}$ | $C_{13}$ | $-3.0543 \times 10^{-4}$ |
| $C_{15}$ | $-1.2923 \times 10^{-4}$ | | | | |

FFS④
| | | | | | |
|---|---|---|---|---|---|
| $C_4$ | $-1.8009 \times 10^{-2}$ | $C_6$ | $-1.6145 \times 10^{-2}$ | $C_8$ | $-7.3044 \times 10^{-4}$ |
| $C_{10}$ | $-1.3764 \times 10^{-4}$ | $C_{11}$ | $-3.8788 \times 10^{-4}$ | $C_{13}$ | $-4.0937 \times 10^{-5}$ |
| $C_{15}$ | $-3.3913 \times 10^{-4}$ | | | | |

FFS⑤
| | | | | | |
|---|---|---|---|---|---|
| $C_4$ | $1.3712 \times 10^{-2}$ | $C_6$ | $2.3152 \times 10^{-2}$ | $C_8$ | $-1.2151 \times 10^{-3}$ |
| $C_{10}$ | $9.0030 \times 10^{-4}$ | $C_{11}$ | $-5.9931 \times 10^{-4}$ | $C_{13}$ | $5.2911 \times 10^{-5}$ |
| $C_{15}$ | $-4.0363 \times 10^{-4}$ | | | | |

FFS⑥
| | | | | | |
|---|---|---|---|---|---|
| $C_4$ | $1.5598 \times 10^{-2}$ | $C_6$ | $1.2737 \times 10^{-1}$ | $C_8$ | $-2.7416 \times 10^{-3}$ |
| $C_{13}$ | $8.2055 \times 10^{-3}$ | | | | |

Displacement and tilt(1)
| X | 0.00 | Y | 0.00 | Z | 0.00 |
|---|---|---|---|---|---|
| α | 28.08 | β | 0.00 | γ | 0.00 |

Displacement and tilt(2)
| X | 0.00 | Y | 0.76 | Z | 4.43 |
|---|---|---|---|---|---|
| α | -19.21 | β | 0.00 | γ | 0.00 |

Displacement and tilt(3)
| X | 0.00 | Y | 7.74 | Z | -1.84 |
|---|---|---|---|---|---|
| α | 9.37 | β | 0.00 | γ | 0.00 |

Displacement and tilt(4)
| X | 0.00 | Y | 13.82 | Z | 0.76 |
|---|---|---|---|---|---|
| α | 66.85 | β | 0.00 | γ | 0.00 |

Displacement and tilt(5)
| X | 0.00 | Y | 0.00 | Z | 4.11 |
|---|---|---|---|---|---|
| α | 24.49 | β | 0.00 | γ | 0.00 |

Displacement and tilt(6)
| X | 0.00 | Y | -2.19 | Z | 2.20 |
|---|---|---|---|---|---|
| α | 72.79 | β | 0.00 | γ | 0.00 |

Displacement and tilt(7)
| X | 0.00 | Y | 1.74 | Z | 1.75 |
|---|---|---|---|---|---|
| α | 115.85 | β | 0.00 | γ | 0.00 |

Displacement and tilt(8)
| X | 0.00 | Y | 1.74 | Z | 1.76 |
|---|---|---|---|---|---|
| α | 86.39 | β | 0.00 | γ | 0.00 |

EXAMPLE 14

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | FFS③ | | (3) | 1.4924 | 57.6 |
| 6 | ∞ (Stop) | | (4) | 1.4924 | 57.6 |
| 7 | FFS④ | | (5) | 1.4924 | 57.6 |
| 8 | FFS⑤ | | (6) | 1.4924 | 57.6 |
| 9 | FFS⑥ | | (7) | | |
| 10 | ∞ (HRP2) | -2.13 | (8) | | |
| Image plane | ∞ | | | | |

FFS①
| | | | | | |
|---|---|---|---|---|---|
| $C_4$ | $3.7054 \times 10^{-2}$ | $C_6$ | $1.6679 \times 10^{-2}$ | $C_8$ | $3.2160 \times 10^{-5}$ |
| $C_{10}$ | $-4.2007 \times 10^{-4}$ | $C_{11}$ | $1.3894 \times 10^{-4}$ | $C_{13}$ | $8.9460 \times 10^{-5}$ |
| $C_{15}$ | $8.9163 \times 10^{-6}$ | | | | |

FFS②
| | | | | | |
|---|---|---|---|---|---|
| $C_4$ | $3.1883 \times 10^{-2}$ | $C_6$ | $3.5792 \times 10^{-3}$ | $C_8$ | $-1.2538 \times 10^{-3}$ |
| $C_{10}$ | $-6.2843 \times 10^{-4}$ | $C_{11}$ | $8.5773 \times 10^{-6}$ | $C_{13}$ | $-1.0024 \times 10^{-4}$ |
| $C_{15}$ | $-7.9627 \times 10^{-5}$ | | | | |

FFS③

-continued

| | | | | | |
|---|---|---|---|---|---|
| $C_4$ | $3.3309 \times 10^{-2}$ | $C_6$ | $6.8480 \times 10^{-3}$ | $C_8$ | $1.6484 \times 10^{-3}$ |
| $C_{10}$ | $-1.4440 \times 10^{-4}$ | $C_{11}$ | $7.6079 \times 10^{-4}$ | $C_{13}$ | $4.0409 \times 10^{-4}$ |
| $C_{15}$ | $5.6887 \times 10^{-5}$ | | | | |

FFS④
| | | | | | |
|---|---|---|---|---|---|
| $C_4$ | $1.9178 \times 10^{-2}$ | $C_6$ | $1.2833 \times 10^{-2}$ | $C_8$ | $7.4411 \times 10^{-4}$ |
| $C_{10}$ | $-3.8584 \times 10^{-4}$ | $C_{11}$ | $1.9273 \times 10^{-5}$ | $C_{13}$ | $-9.5052 \times 10^{-8}$ |
| $C_{15}$ | $2.7615 \times 10^{-5}$ | | | | |

FFS⑤
| | | | | | |
|---|---|---|---|---|---|
| $C_4$ | $-2.4984 \times 10^{-2}$ | $C_6$ | $-2.1249 \times 10^{-2}$ | $C_8$ | $-4.5327 \times 10^{-4}$ |
| $C_{10}$ | $-1.2808 \times 10^{-3}$ | $C_{11}$ | $1.4334 \times 10^{-5}$ | $C_{13}$ | $-9.9058 \times 10^{-5}$ |
| $C_{15}$ | $-3.4862 \times 10^{-5}$ | | | | |

FFS⑥
| | | | | | |
|---|---|---|---|---|---|
| $C_4$ | $-5.4905 \times 10^{-2}$ | $C_6$ | $-1.2779 \times 10^{-1}$ | $C_8$ | $-1.7117 \times 10^{-2}$ |
| $C_{10}$ | $-1.0248 \times 10^{-2}$ | $C_{11}$ | $-8.2754 \times 10^{-4}$ | $C_{13}$ | $-9.4598 \times 10^{-3}$ |
| $C_{15}$ | $-1.0669 \times 10^{-2}$ | | | | |

Displacement and tilt (1)
| X | 0.00 | Y | 2.35 | Z | 0.09 |
|---|---|---|---|---|---|
| α | -4.70 | β | 0.00 | γ | 0.00 |

Displacement and tilt (2)
| X | 0.00 | Y | 0.00 | Z | 1.75 |
|---|---|---|---|---|---|
| α | -27.36 | β | 0.00 | γ | 0.00 |

Displacement and tilt (3)
| X | 0.00 | Y | 5.78 | Z | 3.48 |
|---|---|---|---|---|---|
| α | -0.37 | β | 0.00 | γ | 0.00 |

Displacement and tilt (4)
| X | 0.00 | Y | 11.16 | Z | -1.70 |
|---|---|---|---|---|---|
| α | -46.14 | β | 0.00 | γ | 0.00 |

Displacement and tilt (5)
| X | 0.00 | Y | 0.00 | Z | -6.97 |
|---|---|---|---|---|---|
| α | -26.21 | β | 0.00 | γ | 0.00 |

Displacement and tilt (6)
| X | 0.00 | Y | -2.54 | Z | -5.02 |
|---|---|---|---|---|---|
| α | -81.64 | β | 0.00 | γ | 0.00 |

Displacement and tilt (7)
| X | 0.00 | Y | 2.12 | Z | -3.24 |
|---|---|---|---|---|---|
| α | -111.38 | β | 0.00 | γ | 0.00 |

Displacement and tilt (8)
| X | 0.00 | Y | 2.12 | Z | -3.24 |
|---|---|---|---|---|---|
| α | -110.61 | β | 0.00 | γ | 0.00 |

EXAMPLE 15

| Surface No. | Radius of curvature | Surface separation | Displacement and tilt | Refractive index | Abbe's No. |
|---|---|---|---|---|---|
| Object plane | ∞ | ∞ | | | |
| 1 | ∞ (HRP1) | | | | |
| 2 | FFS① | | (1) | 1.4924 | 57.6 |
| 3 | FFS② | | (2) | 1.4924 | 57.6 |
| 4 | FFS① | | (1) | 1.4924 | 57.6 |
| 5 | FFS③ | | (3) | 1.4924 | 57.6 |
| 6 | ∞ (Stop) | | (4) | 1.4924 | 57.6 |
| 7 | FFS④ | | (5) | 1.4924 | 57.6 |
| 8 | FFS⑤ | | (6) | 1.4924 | 57.6 |
| 9 | FFS⑥ | | (7) | | |
| 10 | ∞ (HRP2) | -2.00 | (8) | | |
| Image plane | ∞ | | | | |

-continued

FFS①

| | | | | | | |
|---|---|---|---|---|---|---|
| $C_4$ | $4.8535 \times 10^{-2}$ | $C_6$ | $1.3761 \times 10^{-2}$ | $C_8$ | $2.7930 \times 10^{-4}$ | |
| $C_{10}$ | $-3.5124 \times 10^{-4}$ | $C_{11}$ | $1.0809 \times 10^{-4}$ | $C_{13}$ | $-7.4720 \times 10^{-5}$ | |
| $C_{15}$ | $-6.2921 \times 10^{-5}$ | | | | | |

FFS②

| | | | | | | |
|---|---|---|---|---|---|---|
| $C_4$ | $4.1383 \times 10^{-2}$ | $C_6$ | $2.3986 \times 10^{-2}$ | $C_8$ | $-3.9155 \times 10^{-5}$ | |
| $C_{10}$ | $-3.1606 \times 10^{-4}$ | $C_{11}$ | $-1.0166 \times 10^{-4}$ | $C_{13}$ | $-2.7883 \times 10^{-4}$ | |
| $C_{15}$ | $-1.7774 \times 10^{-4}$ | | | | | |

FFS③

| | | | | | | |
|---|---|---|---|---|---|---|
| $C_4$ | $4.9345 \times 10^{-2}$ | $C_6$ | $1.2343 \times 10^{-2}$ | $C_8$ | $-1.4156 \times 10^{-4}$ | |
| $C_{10}$ | $-6.8010 \times 10^{-4}$ | $C_{11}$ | $9.3773 \times 10^{-4}$ | $C_{13}$ | $1.3605 \times 10^{-4}$ | |
| $C_{15}$ | $-5.7474 \times 10^{-5}$ | | | | | |

FFS④

| | | | | | | |
|---|---|---|---|---|---|---|
| $C_4$ | $1.8813 \times 10^{-2}$ | $C_6$ | $9.6126 \times 10^{-3}$ | $C_8$ | $-1.1595 \times 10^{-3}$ | |
| $C_{10}$ | $-1.0682 \times 10^{-3}$ | $C_{11}$ | $-7.5707 \times 10^{-6}$ | $C_{13}$ | $-3.7497 \times 10^{-5}$ | |
| $C_{15}$ | $3.3145 \times 10^{-5}$ | | | | | |

FFS⑤

| | | | | | | |
|---|---|---|---|---|---|---|
| $C_4$ | $-2.7646 \times 10^{-2}$ | $C_6$ | $-2.8089 \times 10^{-2}$ | $C_8$ | $-7.8056 \times 10^{-4}$ | |
| $C_{10}$ | $-1.9251 \times 10^{-4}$ | $C_{11}$ | $-3.2528 \times 10^{-6}$ | $C_{13}$ | $2.8135 \times 10^{-5}$ | |
| $C_{15}$ | $7.1783 \times 10^{-5}$ | | | | | |

FFS⑥

| | | | | | | |
|---|---|---|---|---|---|---|
| $C_4$ | $-5.5178 \times 10^{-2}$ | $C_6$ | $-1.9134 \times 10^{-1}$ | $C_8$ | $-1.7197 \times 10^{-2}$ | |
| $C_{10}$ | $-1.0841 \times 10^{-2}$ | $C_{13}$ | $-9.1849 \times 10^{-4}$ | | | |

| Displacement and tilt (1) | | | | | |
|---|---|---|---|---|---|
| X | 0.00 | Y | 5.23 | Z | 1.51 |
| α | −20.43 | β | 0.00 | γ | 0.00 |

| Displacement and tilt (2) | | | | | |
|---|---|---|---|---|---|
| X | 0.00 | Y | −0.24 | Z | 3.27 |
| α | −38.16 | β | 0.00 | γ | 0.00 |

| Displacement and tilt (3) | | | | | |
|---|---|---|---|---|---|
| X | 0.00 | Y | 7.40 | Z | 5.07 |
| α | −12.32 | β | 0.00 | γ | 0.00 |

| Displacement and tilt (4) | | | | | |
|---|---|---|---|---|---|
| X | 0.00 | Y | 8.86 | Z | 4.09 |
| α | −55.96 | β | 0.00 | γ | 0.00 |

| Displacement and tilt (5) | | | | | |
|---|---|---|---|---|---|
| X | 0.00 | Y | 0.00 | Z | −8.72 |
| α | 26.11 | β | 0.00 | γ | 0.00 |

| Displacement and tilt (6) | | | | | |
|---|---|---|---|---|---|
| X | 0.00 | Y | 2.71 | Z | −6.62 |
| α | 77.68 | β | 0.00 | γ | 0.00 |

| Displacement and tilt (7) | | | | | |
|---|---|---|---|---|---|
| X | 0.00 | Y | −2.21 | Z | −5.47 |
| α | 116.77 | β | 0.00 | γ | 0.00 |

| Displacement and tilt (8) | | | | | |
|---|---|---|---|---|---|
| X | 0.00 | Y | −2.21 | Z | −5.47 |
| α | 96.17 | β | 0.00 | γ | 0.00 |

Figure 9:
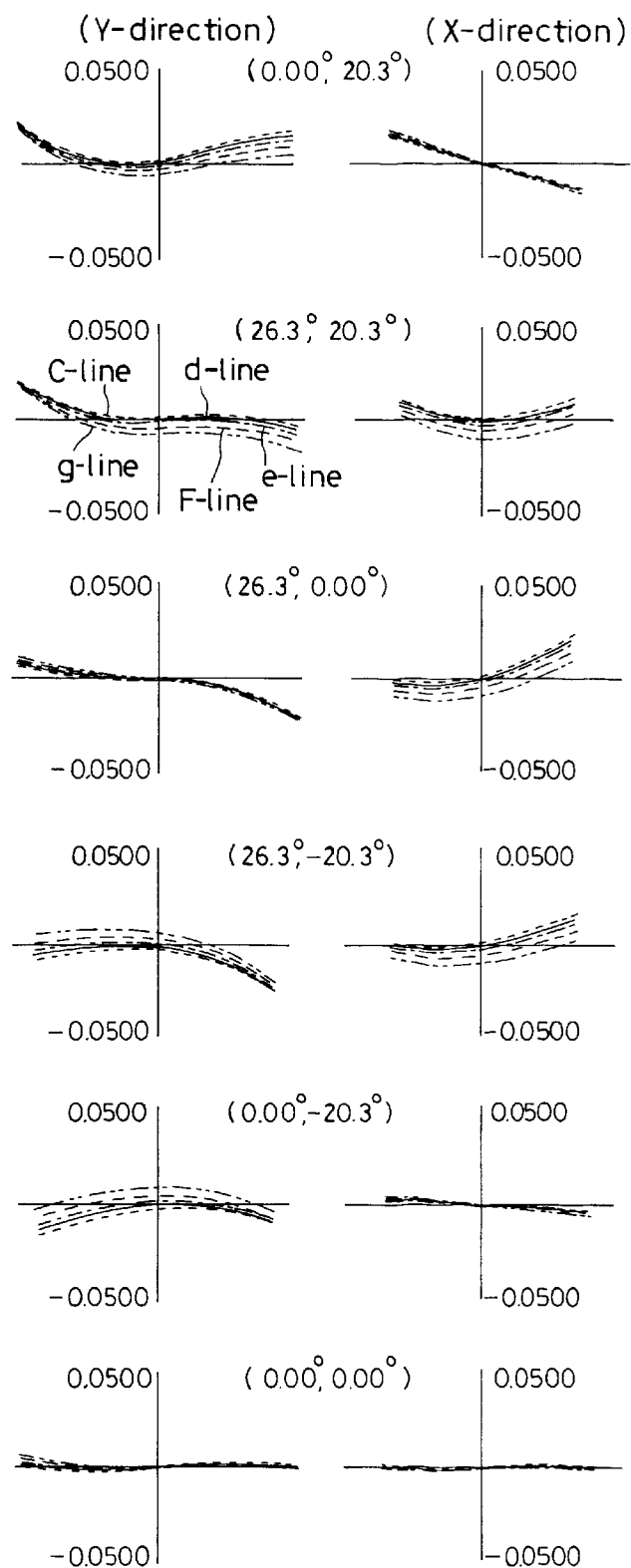
FIG. 9 is an aberrational diagram showing lateral aberrations in the image-forming optical system according to Example 1.

FIG. 9 is an aberrational diagram showing lateral aberrations in the above-described Example 1. In the diagram showing lateral aberrations, the numerals in the parentheses denote [horizontal (X-direction) field angle, vertical (Y-direction) field angle], and lateral aberrations at the field angles are shown.

It should be noted that the values of the conditions (1) to (11) in the above-described Examples 1 to 15 are as follows:

| Cond. | Ex. 1 | Ex. 2 | Ex. 3 | Ex. 4 | Ex. 5 | Ex. 6 | Ex. 7 | Ex. 8 |
|---|---|---|---|---|---|---|---|---|
| (1) | 0.61 | 0.41 | 0.49 | 0.42 | 0.28 | 0.60 | 0.48 | 0.24 |
| (2) | 0.02 | 0.40 | 0.30 | 0.35 | 0.17 | 0.06 | 0.42 | 0.20 |
| (3) | 0.13 | 0.38 | 0.24 | 0.35 | 0.39 | 0.39 | 0.31 | 0.48 |
| (4) | 0.47 | 0.27 | 0.44 | 0.31 | 0.37 | 0.82 | 0.14 | 0.36 |
| (5) | 27.30 | 24.97 | 27.67 | 27.56 | 27.47 | 26.22 | 31.29 | 28.11 |
| (6) | 18.97 | 20.78 | 26.28 | 20.56 | 25.46 | 19.91 | 25.11 | 27.20 |
| (7) | 0.69 | 0.83 | 0.95 | 0.75 | 0.93 | 0.76 | 0.80 | 0.97 |
| (8) | −0.89 | −0.42 | −1.01 | −0.74 | −0.82 | −0.54 | −0.92 | −0.74 |
| (9) | −0.73 | −0.28 | −0.14 | −0.63 | −0.29 | −0.87 | −0.83 | −0.60 |
| (10) | 0.58 | 0.23 | 0.44 | 0.33 | 0.11 | 0.48 | 0.54 | 0.50 |
| (11) | 0.17 | 0.09 | −0.21 | 0.25 | −0.24 | 0.53 | 0.30 | 0.19 |

| Cond. | Ex. 9 | Ex. 10 | Ex. 11 | Ex. 12 | Ex. 13 | Ex. 14 | Ex. 15 |
|---|---|---|---|---|---|---|---|
| (1) | 0.58 | 0.40 | 0.46 | 0.66 | 0.27 | 0.49 | 0.54 |
| (2) | 0.33 | 0.54 | 0.39 | 0.66 | 0.45 | 0.41 | 0.55 |
| (3) | 0.21 | 0.36 | 0.37 | 0.34 | 0.35 | 0.37 | 0.37 |
| (4) | 0.35 | 0.28 | 0.26 | 0.06 | 0.31 | 0.25 | 0.19 |
| (5) | 28.09 | 26.66 | 26.44 | 25.23 | 23.81 | 29.22 | 25.45 |
| (6) | 26.84 | 23.53 | 26.53 | 28.58 | 24.49 | 26.21 | 26.11 |
| (7) | 0.96 | 0.88 | 1.00 | 1.13 | 1.03 | 0.90 | 1.03 |
| (8) | −0.58 | −0.56 | −0.75 | −0.83 | −0.74 | −0.62 | −0.81 |
| (9) | −0.19 | −0.34 | −0.80 | −0.68 | −0.20 | −0.70 | −0.47 |
| (10) | 0.41 | 0.28 | 0.71 | 0.80 | 0.44 | 0.72 | 0.95 |
| (11) | −0.04 | −0.11 | 0.29 | 0.36 | −0.11 | 0.32 | 0.27 |

In the above-described examples, the object-side part of the prism 10, which constitute the image-forming optical system according to the present invention, uses a prism of the type in which there are two or three internal reflections as stated in Examples 1 to 15. It should, however, be noted that prisms usable as the object-side part of the prism 0 in the image-forming optical system according to the present invention are not necessarily limited to the described type. Examples of prisms usable in the present invention include a prism in which there is one internal reflection, and prisms arranged in the same way as in Examples 5, 6, 11, 12, 14 and 15 except that the first reflecting surface 12 and the third reflecting surface 14 are formed from the identical surface. It is also possible to use prisms arranged in the same way as in Examples 5, 6, 11, 12, 14 and 15 except that the second reflecting surface 13 is formed from a surface different from the entrance surface 11.

Incidentally, the above-described image-forming optical system according to the present invention can be used in photographic apparatus, particularly in cameras, in which an object image formed by the image-forming optical system is received with an image pickup device, such as a CCD or a silver halide film, to take a photograph of the object. It is also possible to use the image-forming optical system as an objective optical system of an observation apparatus in which an object image is viewed through an ocular lens, particularly a finder unit of a camera. The image-forming optical system according to the present invention is also usable as an image pickup optical system for optical apparatus using a small-sized image pickup device, e.g. endoscopes. Embodiments in which the present invention is applied to such apparatuses will be described below.

Figure 10:
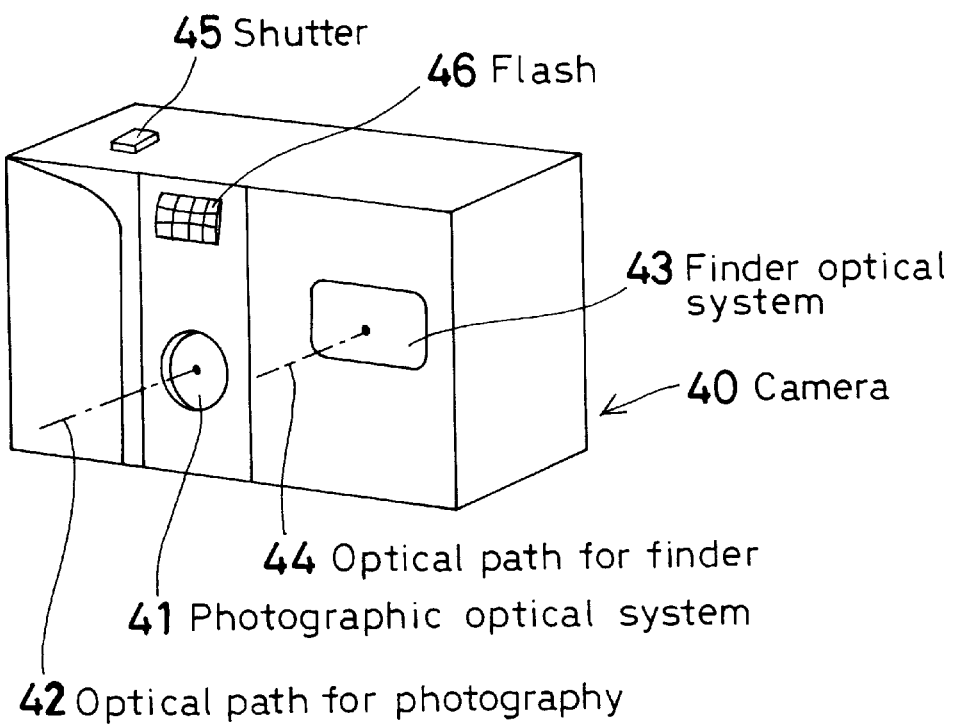
FIG. 10 is a perspective view showing the external appearance of an electronic camera to which an image-forming optical system according to the present invention is applied, as viewed from the front side thereof.
Figure 11:
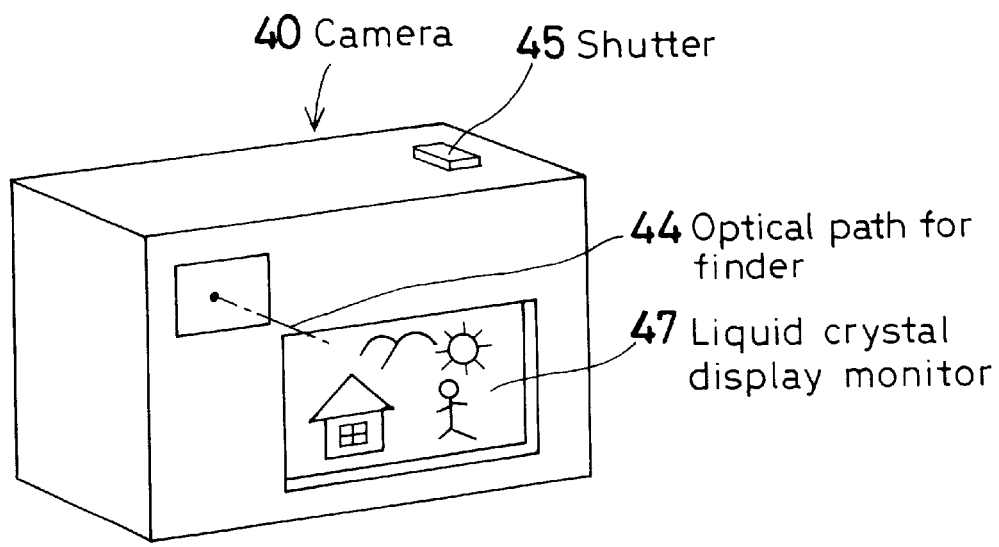
FIG. 11 is a perspective view of the electronic camera shown in FIG. 10, as viewed from the rear side thereof.
Figure 12:
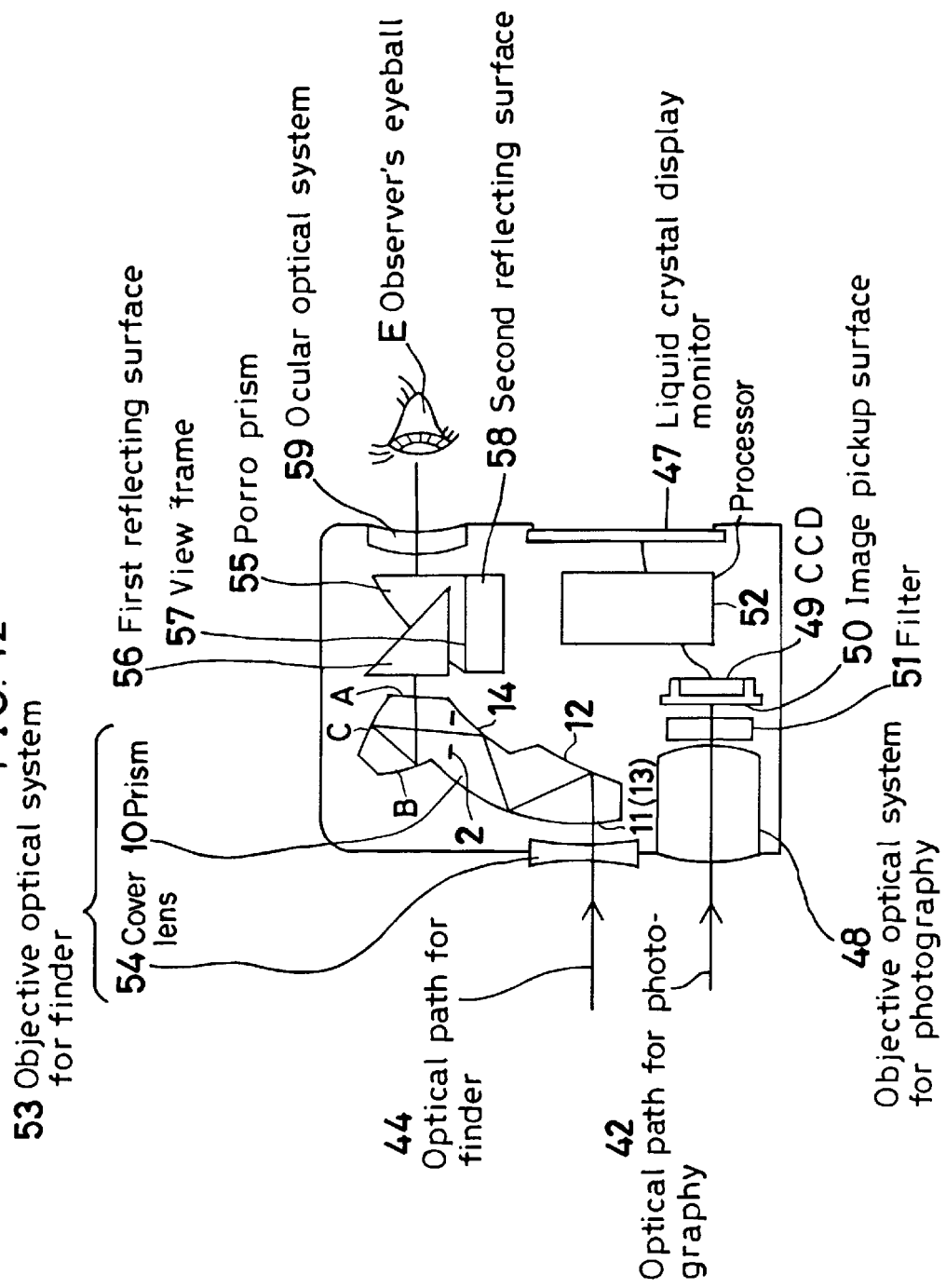
FIG. 12 is a sectional view showing the arrangement of the electronic camera in FIG. 10.

FIGS. 10 to 12 are conceptual views showing an arrangement in which the image-forming optical system according to the present invention is incorporated into an objective optical system in a finder unit of an electronic camera. FIG. 10 is a perspective view showing the external appearance of an electronic camera 40 as viewed from the front side thereof. FIG. 11 is a perspective view of the electronic camera 40 as viewed from the rear side thereof. FIG. 12 is a sectional view showing the arrangement of the electronic camera 40. In the illustrated example, the electronic camera 40 includes a photographic optical system 41 having an optical path 42 for photography, a finder optical system 43 having an optical path 44 for the finder, a shutter 45, a flash 46, a liquid crystal display monitor 47, etc. When the shutter 45, which is placed on the top of the camera 40, is depressed, photography is performed through an objective optical system 48 for photography. An object image produced by the objective optical system 48 for photography is formed on an image pickup surface 50 of a CCD 49 through a filter 51, e.g. a low-pass filter, an infrared cutoff filter, etc. The object image received by the CCD 49 is processed in a processor 52 and displayed as an electronic image on the liquid crystal display monitor 47, which is provided on the rear of the camera 40. The processor 52 is provided with a memory or the like to enable the photographed electronic image to be recorded. It should be noted that the memory may be provided separately from the processor 52. The arrangement may also be such that the photographed electronic image is electronically recorded or written on a floppy disk or the like. The camera 40 may be arranged in the form of a silver halide camera in which a silver halide film is disposed in place of the CCD 49.

Furthermore, an image-forming optical system similar to Example 5, by way of example, is placed in the optical path 44 for the finder as an objective optical system 53 for the finder. In this case, a cover lens 54 having a negative power is provided as a cover member to form a part of the objective optical system 53, thereby enlarging the field angle. It should be noted that the cover lens 54 and a part of the prism 10 that is closer to the object side than the stop 2 constitute a front unit of the objective optical system 53 for the finder, and a part of the prism 10 that is closer to the image side than the stop 2 constitutes a rear unit of the objective optical system 53 for the finder. An object image produced by the objective optical system 53 for the finder is formed on a view frame 57 of a Porro prism 55, which is an image-erecting member. It should be noted that the view frame 57 is placed between a first reflecting surface 56 and second reflecting surface 58 of the Porro prism 55. An ocular optical system 59 is placed behind the Porro prism 55 to lead an erect image to an observer's eyeball E.

In the camera 40, which is arranged as stated above, the objective optical system 53 for the finder can be constructed with a minimal number of optical members. Accordingly, a high-performance and low-cost camera can be realized. In addition, because the optical path of the objective optical system 53 can be folded, the degree of freedom with which the constituent elements can be arranged in the camera increases. This is favorable for design.

Although no mention is made of the arrangement of the objective optical system 48 for photography in the electronic camera 40 shown in FIG. 12, it should be noted that the objective optical system 48 for photography may be formed by using not only a refracting coaxial optical system but also any of the image-forming optical systems, which comprises a single prism 10, according to the present invention.

Figure 13:
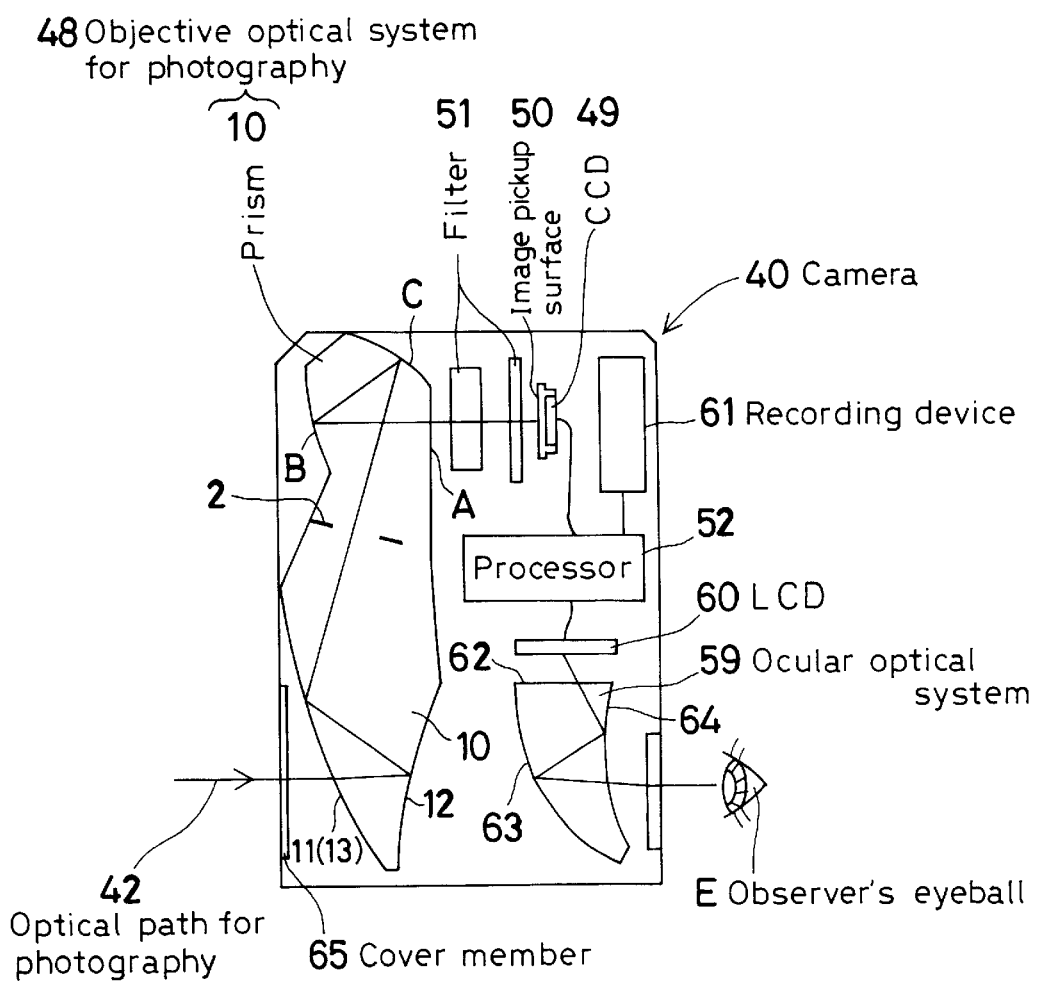
FIG. 13 is a conceptual view of another electronic camera to which an image-forming optical system according to the present invention is applied.

FIG. 13 is a conceptual view showing an arrangement in which an image-forming optical system according to the present invention is incorporated into an objective optical system 48 in a photography part of an electronic camera 40. In this example, an image-forming optical system similar to Example 1 is used in the objective optical system 48 for photography, which is placed in an optical path 42 for photography. An object image produced by the objective optical system 48 for photography is formed on an image pickup surface 50 of a CCD 49 through a filter 51, e.g. a low-pass filter, an infrared cutoff filter, etc. The object image received by the CCD 49 is processed in a processor 52 and displayed in the form of an electronic image on a liquid crystal display device (LCD) 60. The processor 52 also controls a recording device 61 for recording the object image detected by the CCD 49 in the form of electronic information. The image displayed on the LCD 60 is led to an observer's eyeball E through an ocular optical system 59. The ocular optical system 59 is formed from a decentered prism having a configuration similar to that used in the image-forming optical system according to the present invention. In this example, the ocular optical system 59 has three surfaces, i.e. an entrance surface 62, a reflecting surface 63, and a surface 64 serving as both reflecting and refracting surfaces. At least one of the two reflecting surfaces 63 and 64, preferably each of them, is formed from a plane-symmetry free-form surface with only one plane of symmetry that gives a power to a light beam and corrects decentration aberrations. The only one plane of symmetry is formed in approximately the same plane as the only one plane of symmetry of the plane-symmetry free-form surfaces in the prism 10 provided in the objective optical system 48 for photography. The objective optical system 48 for photography may include another lens (positive or negative lens) as a constituent element on the object or image side of the prism 10.

In the camera 40 arranged as stated above, the objective optical system 48 for photography can be constructed with a minimal number of optical members. Accordingly, a high-performance and low-cost camera can be realized. In addition, because all the constituent elements of the optical system can be arranged in the same plane, it is possible to reduce the thickness in a direction perpendicular to the plane in which the constituent elements are arranged.

Although in this example a plane-parallel plate is placed as a cover member 65 of the objective optical system 48 for photography, it is also possible to use a lens having a power as the cover member 65 as in the case of the above-described example.

The surface closest to the object side in the image-forming optical system according to the present invention may be used as a cover member instead of providing a cover member separately. In this example, the entrance surface of the prism 10 is the closest to the object side in the image-forming optical system. In such a case, however, because the entrance surface is decentered with respect to the optical axis, if this surface is placed on the front side of the camera, it gives the illusion that the photographic center of the camera 40 is deviated from the subject when the entrance surface is seen from the subject side (the subject normally feels that photographing is being performed in a direction perpendicular to the entrance surface, as in the case of ordinary cameras). Thus, the entrance surface would give a sense of incongruity. Therefore, in a case where the surface of the image-forming optical system that is closest to the object side is a decentered surface as in this example, it is desirable to provide the cover member 65 (or cover lens 54) from the viewpoint of preventing the subject from feeling incongruous when seeing the entrance surface, and allowing the subject to be photographed with the same feeling as in the case of the existing cameras.

Figure 14A:
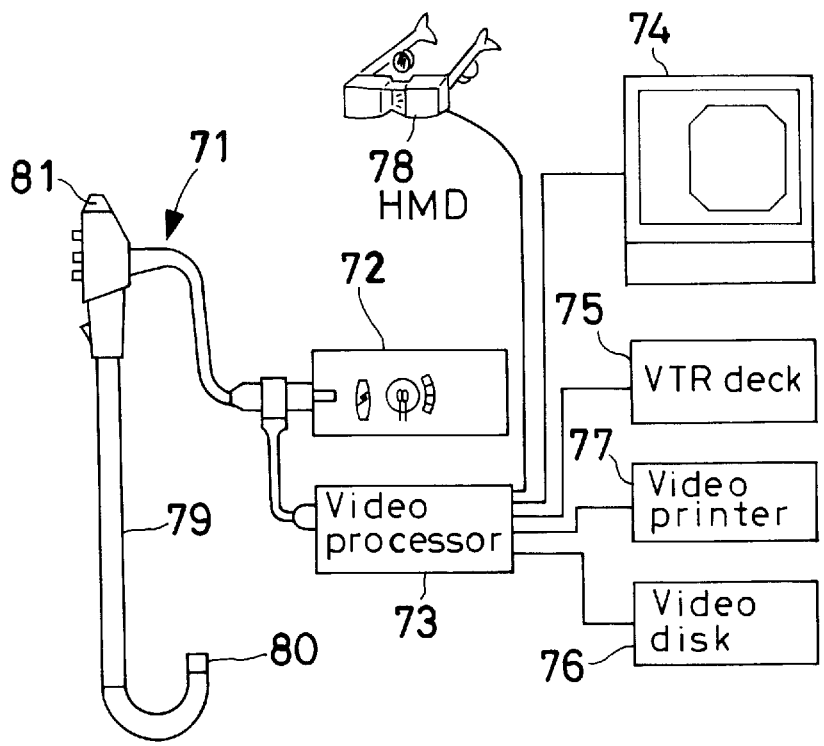
FIGS. 14(a) and 14(b) are a conceptual view of a video endoscope system to which an image-forming optical system according to the present invention is applied.
Figure 14B:
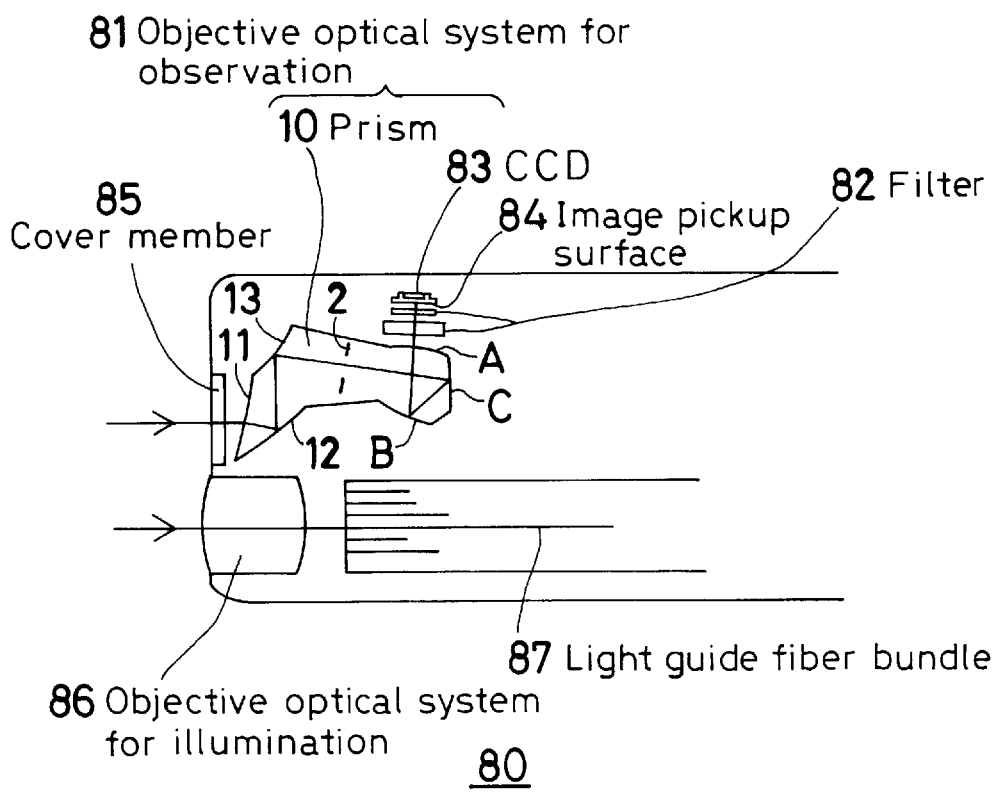

FIG. 14 is a conceptual view showing an arrangement in which an image-forming optical system according to the present invention is incorporated into an objective optical system 81 in an observation system of a video endoscope system. In this case, the objective optical system 81 in the observation system uses an image-forming optical system approximately similar to Example 4. As shown in part (a) of FIG. 14, the video endoscope system includes a video endoscope 71, a light source unit 72 for supplying illuminating light, a video processor 73 for executing processing of signals associated with the video endoscope 71, a monitor 74 for displaying video signals output from the video processor 73, a VTR deck 75 and a video disk 76, which are connected to the video processor 73 to record video signals and so forth, and a video printer 77 for printing out video signals in the form of images. The video endoscope system further includes a head-mounted image display apparatus (HMD) 78. The video endoscope 71 has an insert part 79 with a distal end portion 80. The distal end portion 80 is arranged as shown in part (b) of FIG. 14. A light beam from the light source unit 72 passes through a light guide fiber bundle 87 and illuminates a part to be observed through an objective optical system 86 for illumination. Light from the part to be observed enters an objective optical system 81 for observation through a cover member 85. Thus, an object image is formed by the objective optical system 81. The object image is formed on an image pickup surface 84 of a CCD 83 through a filter 82, e.g. a low-pass filter, an infrared cutoff filter, etc. Furthermore, the object image is converted into a video signal by the CCD 83. The video signal is displayed directly on the monitor 74 by the video processor 73, which is shown in part (a) of FIG. 14. In addition, the video signal is recorded in the VTR deck 75 and on the video disk 76 and also printed out in the form of an image from the video printer 77. In addition, the object image is displayed on the image display device of the HMD 78, thereby allowing a person wearing the HMD 78 to observe the displayed image.

The endoscope arranged as stated above can be constructed with a minimal number of optical members. Accordingly, a high-performance and low-cost endoscope can be realized. Moreover, because the constituent portions of the single prism 10 of the objective optical system 81 in the observation system are arranged in series in the direction of the longitudinal axis of the endoscope, the above-described advantageous effects can be obtained without hindering the achievement of a reduction in the diameter of the endoscope.

Figure 15:
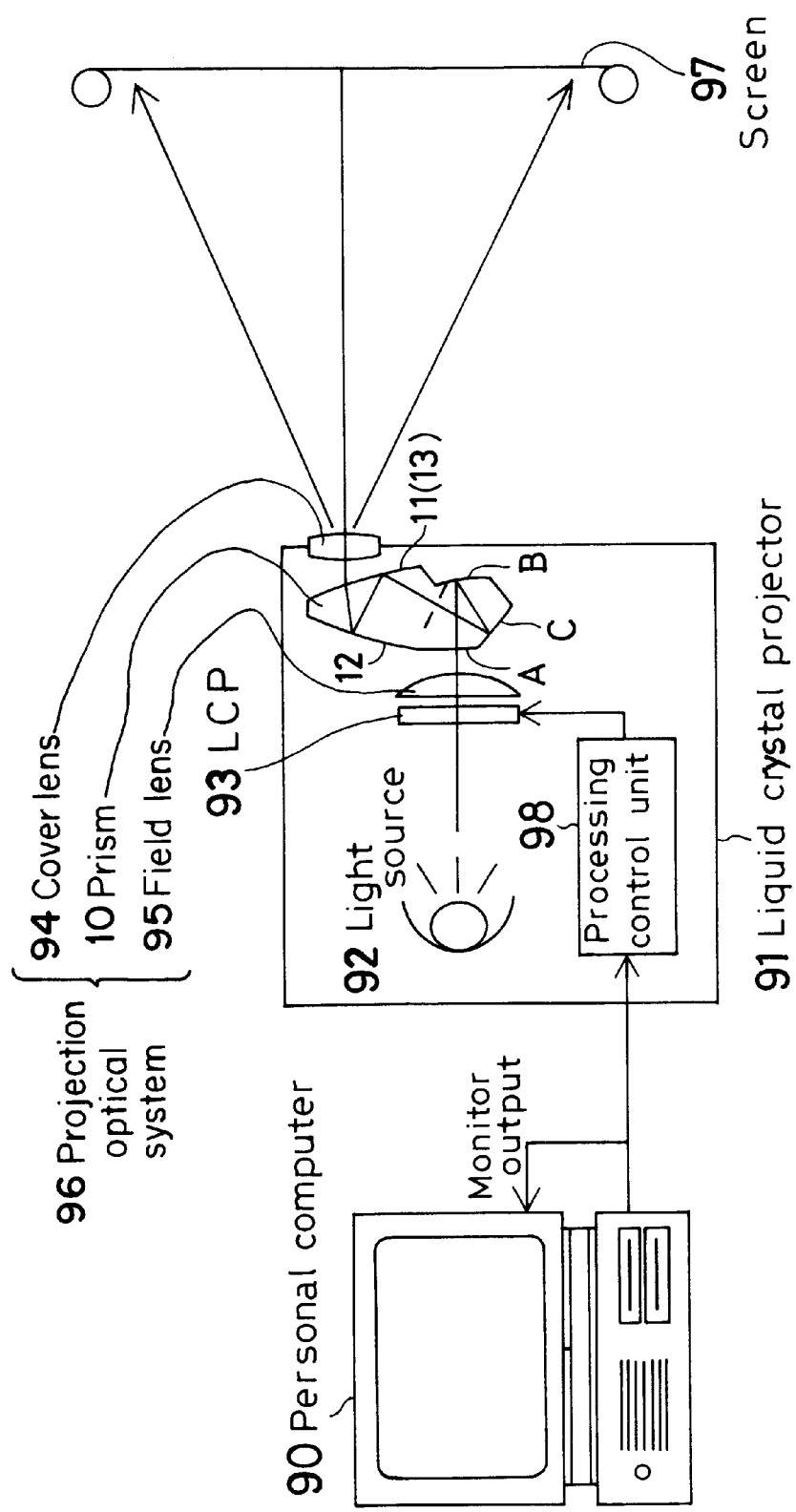
FIG. 15 is a conceptual view showing an arrangement in which a prism optical system according to the present invention is applied to a projection optical system of a presentation system.

Incidentally, the image-forming optical system can also be used as a projection optical system by reversing the optical path. FIG. 15 is a conceptual view showing an arrangement in which a prism optical system according to the present invention is used in a projection optical system 96 of a presentation system formed by combining together a personal computer 90 and a liquid crystal projector 91. In this example, an image-forming optical system similar to Example 1 except that the optical path is reverse to that in Example 1 is used in the projection optical system 96. Referring to FIG. 15, image and manuscript data prepared on the personal computer 90 is branched from a monitor output and delivered to a processing control unit 98 in the liquid crystal projector 91. In the processing control unit 98 of the liquid crystal projector 91, the input data is processed and output to a liquid crystal panel (LCP) 93. The liquid crystal panel 93 displays an image corresponding to the input image data. Light from a light source 92 is applied to the liquid crystal panel 93. The amount of light transmitted by the liquid crystal panel 93 is determined by the gradation of the image displayed on the liquid crystal panel 93. Light from the liquid crystal panel 93 is projected on a screen 97 through a projection optical system 96 comprising a field lens 95 placed immediately in front of the liquid crystal panel 93, a prism 10 constituting the image-forming optical system according to the present invention, and a cover lens 94 which is a positive lens.

The projector arranged as stated above can be constructed with a minimal number of optical members. Accordingly, a high-performance and low-cost projector can be realized. In addition, the projector can be constructed in a compact form.

Figure 16:
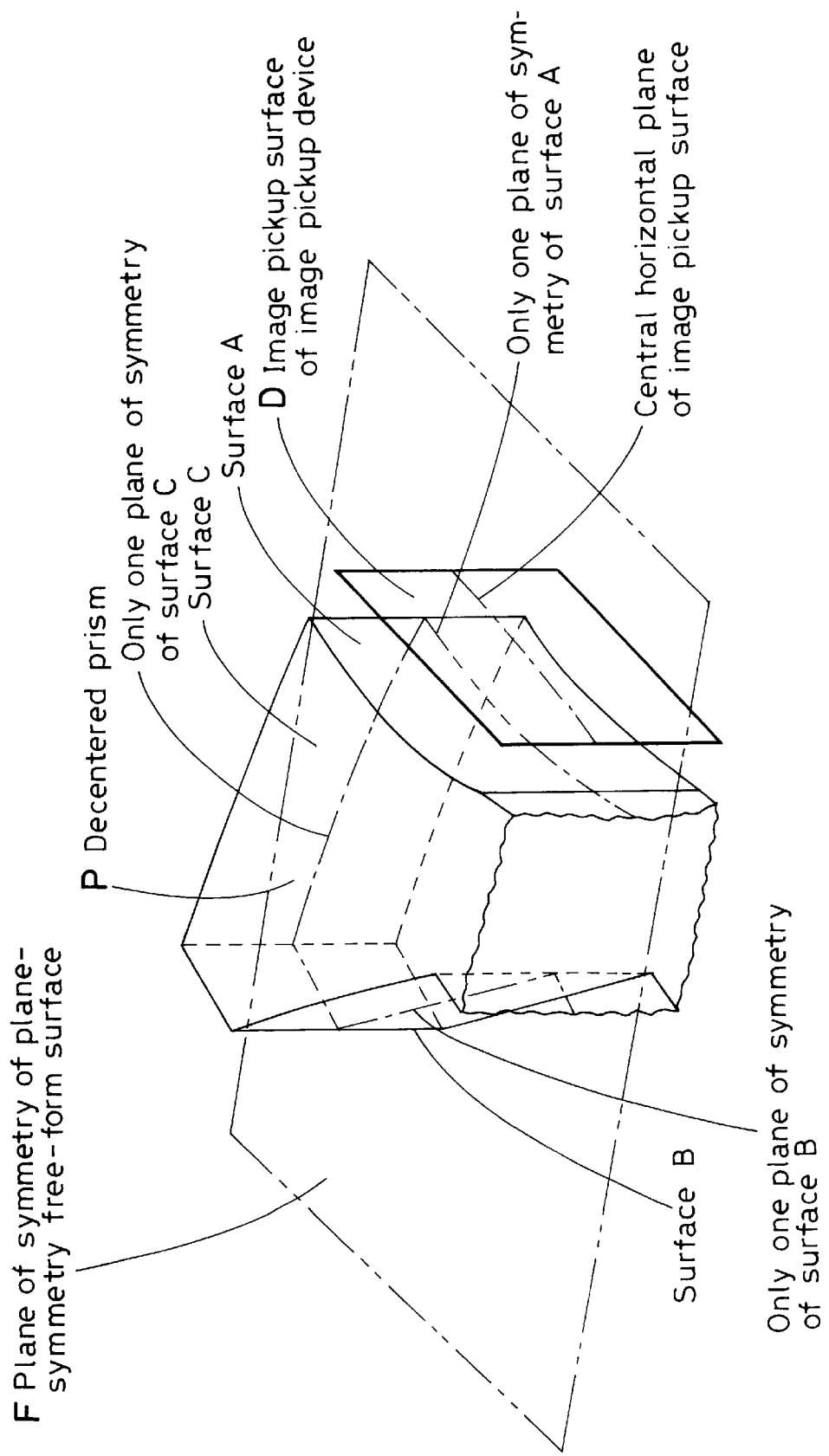
FIG. 16 is a diagram showing a desirable arrangement for an image-forming optical system according to the present invention when it is placed in front of an image pickup device.
Figure 17:
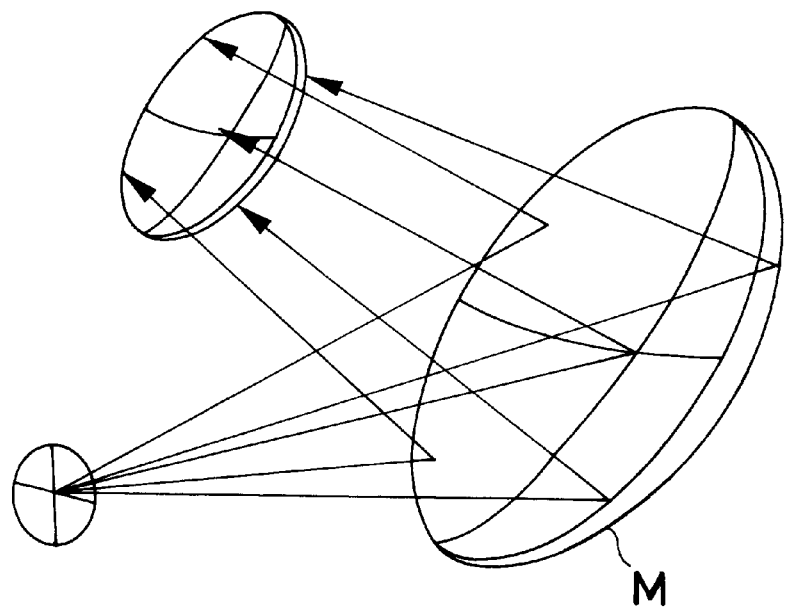
FIG. 17 is a conceptual view for describing curvature of field produced by a decentered reflecting surface.
Figure 18:
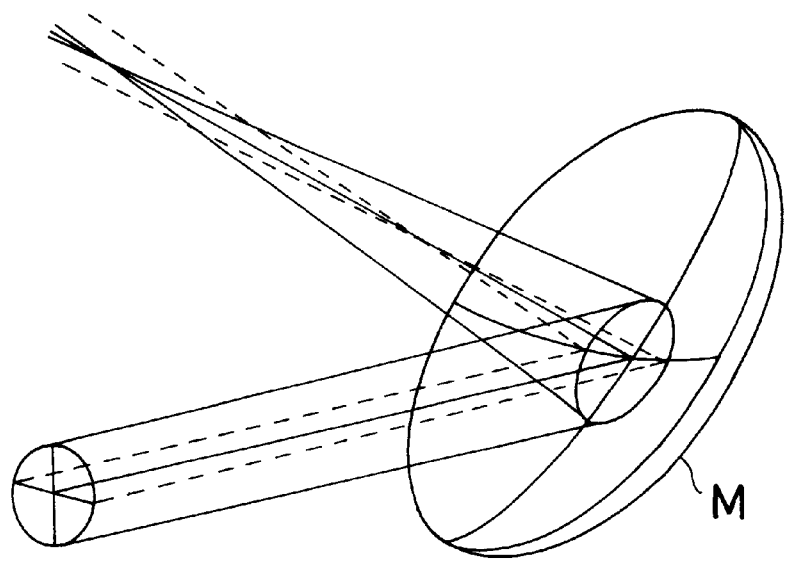
FIG. 18 is a conceptual view for describing astigmatism produced by a decentered reflecting surface.
Figure 19:
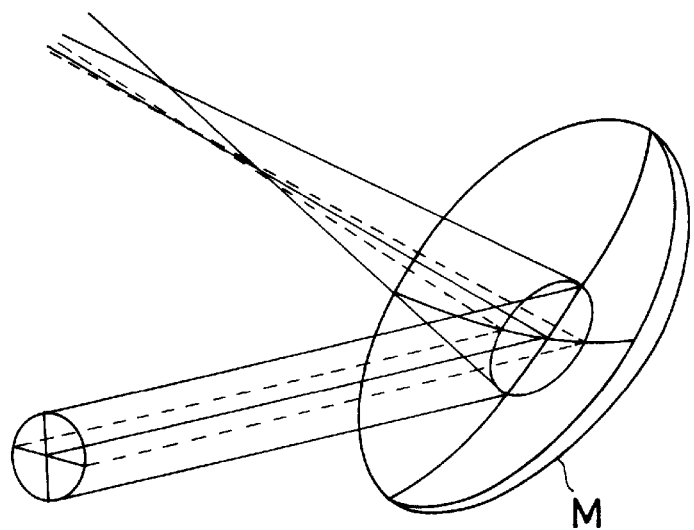
FIG. 19 is a conceptual view for describing coma produced by a decentered reflecting surface.
Figure 20:
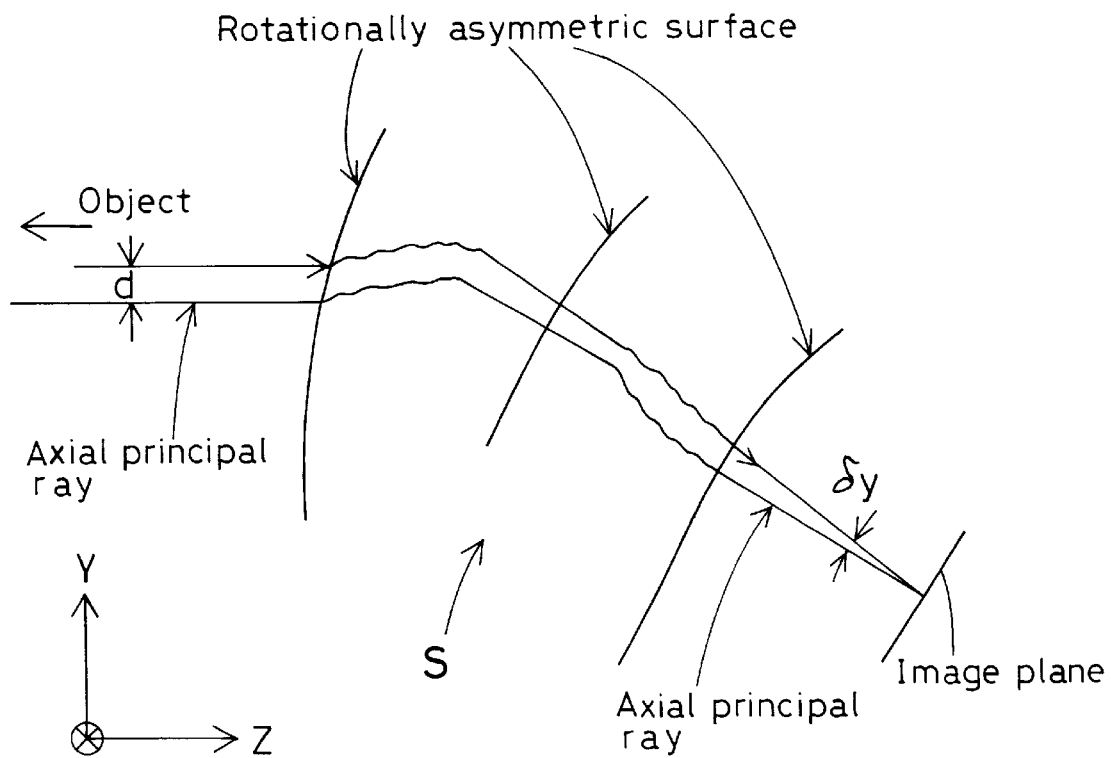
FIG. 20 is a diagram for describing the definition of the power of a decentered optical system and the power of a decentered optical surface.

FIG. 16 is a diagram showing a desirable arrangement for the image-forming optical system according to the present invention when the image-forming optical system is placed in front of an image pickup device, e.g. a CCD, or a filter. In the figure, a decentered prism P is a prism included in the image-forming optical system according to the present invention. When the image pickup surface D of an image pickup device forms a quadrangle as shown in the figure, it is desirable from the viewpoint of forming a beautiful image to place the decentered prism P so that the plane F of symmetry of a plane-symmetry free-form surface provided in the decentered prism P is parallel to at least one of the sides forming the quadrangular image pickup surface D.

When the image pickup surface D has a shape in which each of the four interior angles is approximately 90 degrees, such as a square or a rectangle, it is desirable that the plane F of symmetry of the plane-symmetry free-form surface should be parallel to two sides of the image pickup surface D that are parallel to each other. It is more desirable that the plane F of symmetry should lie at the middle between two parallel sides and coincide with a position where the image pickup surface D is in a symmetry between the right and left halves or between the upper and lower halves. The described arrangement enables the required assembly accuracy to be readily obtained when the image-forming optical system is incorporated into an apparatus, and is useful for mass-production.

When a plurality or all of the optical surfaces constituting the decentered prism P, i.e. the entrance surface, the first reflecting surface, the surface C, the surface B, the surface A, and so forth, are plane-symmetry free-form surfaces, it is desirable from the viewpoint of design and aberration correcting performance to arrange the decentered prism P so that the planes of symmetry of the plurality or all of the optical surfaces are in the same plane F. In addition, it is desirable that the plane F of symmetry and the image pickup surface D should be in the above-described relationship.

As will be clear from the foregoing description, the present invention makes it possible to provide a high-performance and low-cost image-forming optical system with a minimal number of constituent optical elements. In addition, it is possible to provide a high-performance image-forming optical system that is made compact and thin by folding an optical path using reflecting surfaces arranged to minimize the number of reflections.

I claim:

1. An image-forming optical system having a positive refracting power as a whole for forming an object image, said image-forming optical system comprising:
  at least one prism formed from a medium having a refractive index (n) larger than 1.3 (n>1.3);
  said image-forming optical system having a pupil in said prism and being adapted to lead light rays from an object to an image plane without forming an image in said prism;
  wherein said prism has at least four optical surfaces that transmit or reflect a light beam;
  said at least four optical surfaces including a first optical surface, a second optical surface and a third optical surface provided in order from said image plane;

at least one of said second optical surface and said third optical surface having a curved surface configuration that gives a power to the light beam;

said curved surface configuration having a rotationally asymmetric surface configuration that corrects aberrations due to decentration;

said first optical surface having a transmitting action by which rays internally reflected from said second optical surface are allowed to exit from said prism;

said second optical surface having a reflecting action to reflect rays internally reflected from said third optical surface; and said third optical surface having a reflecting action, wherein rays incident on said third optical surface and the rays reflected from said second optical surface intersect each other.

2. An image-forming optical system according to claim 1, wherein both said third optical surface and said second optical surface have a rotationally asymmetric surface configuration that gives a power to a light beam and corrects aberrations due to decentration.

3. An image-forming optical system according to claim 2, wherein the rotationally asymmetric surface configurations of both said third optical surface and said second optical surface are plane-symmetry free-form surfaces each having only one plane of symmetry.

4. An image-forming optical system according to claim 3, wherein the only one plane of symmetry of the plane-symmetry free-form surface that forms said third optical surface and the only one plane of symmetry of the plane-symmetry free-form surface that forms said second optical surface are formed in a same plane.

5. An image-forming optical system according to claim 1, wherein the rotationally asymmetric surface configuration of at least one of said third optical surface and said second optical surface is a plane-symmetry free-form surface having only one plane of symmetry.

6. An image-forming optical system according to claim 1, wherein said first optical surface has a rotationally asymmetric surface configuration that gives a power to a light beam and corrects aberrations due to decentration.

7. An image-forming optical system according to claim 6, wherein the rotationally asymmetric surface configuration of said first optical surface is a plane-symmetry free-form surface having only one plane of symmetry.

8. An image-forming optical system according to claim 1, wherein a rotationally asymmetric surface placed in an object-side part of said prism, exclusive of said first, second and third optical surfaces, is a plane-symmetry free-form surface having only one plane of symmetry.

9. An image-forming optical system according to claim 8, wherein the object-side part of said prism and an image-side part of said prism including said first, second and third optical surfaces each have at least one plane-symmetry free-form surface having only one plane of symmetry, and the only one plane of symmetry of the at least one plane-symmetry free-form surface in said object-side part and the only one plane of symmetry of the at least one plane-symmetry free-form surface in said image-side part are placed in a same plane.

10. An image-forming optical system according to claim 1, wherein said pupil is placed between an object-side part of said prism, exclusive of said first, second and third optical surfaces, and an image-side part of said prism including said first, second and third optical surfaces, and said image-side part is placed between said pupil and said image plane.

11. An image-forming optical system according to claim 10, wherein a stop is placed on said pupil.

12. An image-forming optical system according to claim 1, wherein an object-side part of said prism, exclusive of said first, second and third optical surfaces, has at least two reflecting surfaces each having a curved surface configuration that gives a power to a light beam.

13. An image-forming optical system having a positive refracting power as a whole for forming an object image, said image-forming optical system comprising:

at least one prism formed from a medium having a refractive index (n) larger than 1.3 (n>1.3);

said image-forming optical system having a pupil in said prism and being adapted to lead light rays from an object to an image plane without forming an image in said prism;

wherein said prism has at least four optical surfaces that transmit or reflect a light beam;

said at least four optical surfaces including a first optical surface, a second optical surface and a third optical surface provided in order from said image plane; at least one of said second optical surface and said third optical surface having a curved surface configuration that gives a power to the light beam;

said curved surface configuration having a rotationally asymmetric surface configuration that corrects aberrations due to decentration;

said first optical surface having a transmitting action by which rays internally reflected from said second optical surface are allowed to exit from said prism;

said second optical surface having a reflecting action to reflect rays internally reflected from said third optical surface; and said third optical surface having a reflecting action, wherein rays incident on said third optical surface and the rays reflected from said second optical surface intersect each other; and wherein an object-side part of said prism, exclusive of said first, second and third optical surfaces, comprises two optical surfaces, which are an entrance surface serving as both a reflecting surface and a transmitting surface, and a reflecting surface.

14. An image-forming optical system according to claim 1, wherein an object-side part of said prism, exclusive of said first, second and third optical surfaces, comprises an entrance surface having a transmitting action by which a light beam is allowed to enter said prism, and two reflecting surfaces that give a power to a light beam.

15. An image-forming optical system according to claim 14, wherein said object-side part of said prism is arranged such that said two reflecting surfaces of said object-side part are placed to face each other across said medium, and said entrance surface and said two reflecting surfaces form a Z-shaped optical path.

16. An image-forming optical system according to any one of claims 1 to 12, wherein an object-side part of said prism, exclusive of said first, second and third optical surfaces a comprises three optical surfaces, which are an entrance surface serving as both a reflecting surface and a transmitting surface, and two reflecting surfaces.

17. An image-forming optical system according to any one of claims 1 to 15, wherein when a decentration direction of said image-forming optical system is a Y-axis direction, and a plane parallel to an axial principal ray is a YZ-plane, and further a direction perpendicularly intersecting the YZ-plane is an X-axis direction, at least one of the following conditions is satisfied:

$$0<Pxb/Px<2 \quad (1)$$

$$-0.5<Pyb/Py<2 \quad (2)$$

where Pxb and Pyb are powers in the X and Y-axis directions of said second optical surface, and Px and Py are powers in the X and Y-axis directions of said prism.

18. An image-forming optical system according to any one of claims 1 to 15, wherein when a decentration direction of said image-forming optical system is a Y-axis direction, and a plane parallel to an axial principal ray is a YZ-plane, and further a direction perpendicularly intersecting the YZ-plane is an X-axis direction, at least one of the following conditions is satisfied:

$$0<Pxc/Px<2 \quad (3)$$

$$0<Pyc/Py<2 \quad (4)$$

where Pxc and Pyc are powers in the X and Y-axis directions of said third optical surface, and Px and Py are powers in the X and Y-axis directions of said prism.

19. An image-forming optical system according to any one of claims 1 to 15, wherein at least one of the following conditions is satisfied:

$$5°<\alpha b<45° \quad (5)$$

$$5°<\alpha c<45° \quad (6)$$

where αb and αc are incident angles of an axial principal ray on said second and third optical surfaces, respectively.

20. An image-forming optical system according to any one of claims 1 to 15, wherein the following conditions is satisfied:

$$0.2<\alpha bc<3 \quad (7)$$

where αbc is a ratio of αc/αb of an incident angle αc of an axial principal ray on said third optical surface to an incident angle αb of the axial principal ray on said second optical surface.

21. An image-forming optical system according to any one of claims 12 to 15, wherein when a decentration direction of said image-forming optical system is a Y-axis direction, and a plane parallel to an axial principal ray is a YZ-plane, and further a direction perpendicularly intersecting the YZ-plane is an X-axis direction, at least one of the following conditions is satisfied:

$$-5<Px1/Px<0 \quad (8)$$

$$-4<Py1/Py<0 \quad (9)$$

where Px1 and Py1 are powers in the X and Y-axis directions of a first reflecting surface of the reflecting surfaces in said object-side part of said prism as counted from an object side of said prism, and Px and Py are powers in the X and Y-axis directions of said prism.

22. An image-forming optical system according to any one of claims 12 to 15, wherein when a decentration direction of said image-forming optical system is a Y-axis direction, and a plane parallel to an axial principal ray is a YZ-plane, and further a direction perpendicularly intersecting the YZ-plane is an X-axis direction, at least one of the following conditions is satisfied:

$$-2<Px2/Px<4 \quad (10)$$

$$-2<Py2/Py<2 \quad (11)$$

where Px2 and Py2 are powers in the X and Y-axis directions of a second reflecting surface of the reflecting surfaces in said object-side part of said prism as counted from an object side of said prism, and Px and Py are powers in the X and Y-axis directions of said prism.

23. A finder optical system comprising:

said image-forming optical system according to any one of claims 1 to 15, said image-forming optical system being provided as a finder objective optical system;

an image-inverting optical system for erecting an object image formed by said finder objective optical system; and an ocular optical system.

24. A camera apparatus comprising:

said finder optical system according to claim 23; and an objective optical system for photography provided in parallel to said finder optical system.

25. An image pickup optical system comprising:

said image-forming optical system according to any one of claims 1 to 15; and an image pickup device placed in an image plane formed by said image-forming optical system.

26. A camera apparatus comprising:

said image-forming optical system according to any one of claims 1 to 15, said image-forming optical system being provided as an objective optical system for photography; and a finder optical system placed in one of an optical path separate from an optical path of said objective optical system for photography and an optical path split from the optical path of said objective optical system for photography.

27. An electronic camera apparatus comprising:

said image-forming optical system according to any one of claims 1 to 15;

an image pickup device placed in an image plane formed by said image forming optical system;

a recording medium for recording image information received by said image pickup device; and an image display device that receives image information from one of said recording medium and said image pickup device to form an image for observation.

28. An endoscope system comprising:

an observation system having said image-forming optical system according to any one of claims 1 to 15 and an image transmitting member for transmitting an image formed by said image-forming optical system along a longitudinal axis; and an illumination system having an illuminating light source and an illuminating light transmitting member for transmitting illuminating light from said illuminating light source along said longitudinal axis.

* * * * *